US011441181B2

(12) United States Patent
Tazi et al.

(10) Patent No.: US 11,441,181 B2
(45) Date of Patent: Sep. 13, 2022

(54) MIRNA-124 AS A BIOMARKER

(71) Applicants: ABIVAX, Paris (FR); CENTRE NATIONAL DE LA RECHERCHE SCIENTIFIQUE, Paris (FR); UNIVERSITE DE MONTPELLIER, Montpellier (FR); INSTITUT CURIE, Paris (FR)

(72) Inventors: Jamal Tazi, Clapiers (FR); Didier Scherrer, Castelnau le Lez (FR); Aude Garcel, Le Cres (FR); Noëlie Campos, Le Cres (FR); Romain Najman, L'hay les Roses (FR); Florence Mahuteau-Betzer, Saint Remy les Chevreuse (FR)

(73) Assignees: ABIVAX, Paris (FR); CENTRE NATIONAL DE LA RECHERCHE, Paris (FR); UNIVERSITE DE MONTPELLIER, Montpellier (FR); INSTITUT CURIE, Paris (FR)

( * ) Notice: Subject to any disclaimer, the term of this patent is extended or adjusted under 35 U.S.C. 154(b) by 596 days.

(21) Appl. No.: 14/761,674

(22) PCT Filed: Jan. 17, 2014

(86) PCT No.: PCT/IB2014/058359
§ 371 (c)(1),
(2) Date: Jul. 17, 2015

(87) PCT Pub. No.: WO2014/111892
PCT Pub. Date: Jul. 24, 2014

(65) Prior Publication Data
US 2015/0361491 A1 Dec. 17, 2015

(30) Foreign Application Priority Data

Jan. 17, 2013 (EP) ..................................... 13305053

(51) Int. Cl.
*C12Q 1/68* (2018.01)
*C12Q 1/6876* (2018.01)
*C12Q 1/70* (2006.01)

(52) U.S. Cl.
CPC ............. *C12Q 1/6876* (2013.01); *C12Q 1/70* (2013.01); *C12Q 2600/106* (2013.01); *C12Q 2600/112* (2013.01); *C12Q 2600/136* (2013.01); *C12Q 2600/158* (2013.01); *C12Q 2600/178* (2013.01)

(58) Field of Classification Search
CPC .. C12Q 1/6876; C12Q 1/70; C12Q 2600/106; C12Q 2600/112; C12Q 2600/136; C12Q 2600/158; C12Q 2600/178
See application file for complete search history.

(56) References Cited

U.S. PATENT DOCUMENTS

| | | | |
|---|---|---|---|
| 2,605,182 A | 7/1952 | Peterson | |
| 4,434,290 A | 2/1984 | Bisagni et al. | |
| 4,738,710 A | 4/1988 | Serban et al. | |
| 6,180,632 B1 | 1/2001 | Myers et al. | |
| 7,019,147 B1 | 3/2006 | Barth et al. | |
| 9,061,999 B2 | 6/2015 | Tazi et al. | |
| 9,108,919 B2 | 8/2015 | Roux et al. | |
| 9,145,367 B2 | 9/2015 | Tazi et al. | |
| 9,637,475 B2 | 5/2017 | Roux et al. | |
| 10,017,498 B2 | 7/2018 | Tazi et al. | |
| 10,253,020 B2 | 4/2019 | Tazi et al. | |
| 10,435,370 B2 | 10/2019 | Tazi et al. | |
| 10,683,284 B2 | 6/2020 | Tazi et al. | |
| 2003/0207886 A1 | 11/2003 | Plucker et al. | |
| 2004/0038969 A1 | 2/2004 | Doherty et al. | |
| 2005/0085482 A1 | 4/2005 | Ramurthy et al. | |
| 2005/0119225 A1 | 6/2005 | Schumacher et al. | |
| 2006/0089380 A1 | 4/2006 | Barnham et al. | |
| 2008/0161353 A1 | 7/2008 | Barnham et al. | |
| 2008/0318984 A1 | 12/2008 | Verkman et al. | |
| 2010/0167948 A1* | 7/2010 | Krichevsky | C12Q 1/6883 506/9 |
| 2011/0003843 A1 | 1/2011 | Lejeune et al. | |
| 2011/0111976 A1* | 5/2011 | Fare | C12Q 1/6883 506/9 |
| 2012/0277230 A1 | 11/2012 | Roux et al. | |
| 2012/0283265 A1 | 11/2012 | Tazi et al. | |
| 2012/0329796 A1 | 12/2012 | Tazi et al. | |
| 2013/0267703 A1 | 10/2013 | Tazi et al. | |
| 2014/0051085 A1* | 2/2014 | Ding | C12N 5/0619 435/6.12 |
| 2014/0080831 A1 | 3/2014 | Roux et al. | |
| 2014/0288120 A1 | 9/2014 | Tazi et al. | |
| 2015/0225796 A1* | 8/2015 | Snijders | C12Q 1/6886 435/6.11 |
| 2015/0299129 A1 | 10/2015 | Roux et al. | |
| 2015/0307478 A1 | 10/2015 | Tazi et al. | |
| 2015/0361491 A1 | 12/2015 | Tazi et al. | |
| 2016/0041153 A1* | 2/2016 | Brown | G01N 33/5308 435/7.23 |
| 2017/0204063 A1 | 7/2017 | Tazi et al. | |
| 2018/0030078 A1 | 2/2018 | Scherrer et al. | |
| 2019/0077760 A1 | 3/2019 | Rabe et al. | |
| 2019/0382347 A1 | 12/2019 | Scherrer et al. | |
| 2020/0062713 A1 | 2/2020 | Rabe et al. | |

FOREIGN PATENT DOCUMENTS

DE 958 647 C 2/1957
EP 0 394 112 A2 10/1990
(Continued)

OTHER PUBLICATIONS

Tatro et al in "Evidence for Alteration of Gene Regulatory Networks through MicroRNAs of the HIV-Infected Brain: Novel Analysis of Retrospective Cases" (PLoSone vol. 5, No. 4, e10337, pp. 1-13, published Apr. 20, 2010) . (Year: 2010).*
(Continued)

*Primary Examiner* — Catherine S Hibbert
(74) *Attorney, Agent, or Firm* — Oliff PLC

(57) ABSTRACT

A use of at least one miRNA, said at least one miRNA being miR-124, as a biomarker, in particular of a viral infection, or of an efficacy of a therapeutic treatment of said viral infection.

14 Claims, No Drawings
Specification includes a Sequence Listing.

(56) References Cited

FOREIGN PATENT DOCUMENTS

| | | |
|---|---|---|
| EP | 1 897 914 A1 | 3/2008 |
| EP | 2 075 309 A2 | 7/2009 |
| EP | 2 266 972 A1 | 12/2010 |
| EP | 2 465 502 A1 | 6/2012 |
| EP | 2 757 161 A1 | 7/2014 |
| EP | 2 974 729 A1 | 1/2016 |
| EP | 3 059 236 A1 | 8/2016 |
| FR | 2 387 229 A1 | 11/1978 |
| FR | 2 436 786 A1 | 4/1980 |
| FR | 2 627 493 A1 | 8/1989 |
| FR | 2 645 861 A1 | 10/1990 |
| FR | 2 849 474 A3 | 7/2004 |
| FR | 2 859 474 A1 | 3/2005 |
| FR | 2 859 475 A1 | 3/2005 |
| GB | 585362 A | 2/1947 |
| JP | H09-508642 A | 9/1997 |
| JP | 2005-507365 A | 3/2005 |
| JP | 2006-504646 A | 2/2006 |
| JP | 2006-519846 A | 8/2006 |
| JP | 2008-519814 A | 6/2008 |
| JP | 2009-174368 A | 8/2009 |
| JP | 6378802 B2 | 8/2018 |
| WO | 95/21613 A1 | 8/1995 |
| WO | 00/59875 A2 | 10/2000 |
| WO | 2002/074726 A2 | 9/2002 |
| WO | 2003/037866 A1 | 5/2003 |
| WO | 2004/007461 A1 | 1/2004 |
| WO | 2004/078731 A1 | 9/2004 |
| WO | 2004/080463 A1 | 9/2004 |
| WO | 2005/023255 A2 | 3/2005 |
| WO | 2005/051302 A2 | 6/2005 |
| WO | 2005/112930 A1 | 12/2005 |
| WO | 2006/051311 A1 | 5/2006 |
| WO | 2006/081444 A2 | 8/2006 |
| WO | 2007/000876 A1 | 1/2007 |
| WO | 2007/042899 A2 | 4/2007 |
| WO | 2007/147217 A1 | 12/2007 |
| WO | 2008/003864 A1 | 1/2008 |
| WO | 2008/008234 A1 | 1/2008 |
| WO | 2008/089459 A1 | 7/2008 |
| WO | 2008/101935 A2 | 8/2008 |
| WO | 2008/115870 A2 | 9/2008 |
| WO | 2008/143440 A2 | 11/2008 |
| WO | 2009/021696 A1 | 2/2009 |
| WO | 2009/023844 A2 | 2/2009 |
| WO | 2009/029617 A1 | 3/2009 |
| WO | 2009/085234 A2 | 7/2009 |
| WO | 2009/087238 A2 | 7/2009 |
| WO | 2009/132273 A2 | 10/2009 |
| WO | 2010/107965 A1 | 9/2010 |
| WO | 2010/129451 A1 | 11/2010 |
| WO | 2010/143168 A2 | 12/2010 |
| WO | 2010/143169 A2 | 12/2010 |
| WO | 2010/143170 A2 | 12/2010 |
| WO | 2010/151755 A2 | 12/2010 |
| WO | 2011/057003 A2 | 5/2011 |
| WO | 2012/080953 A1 | 6/2012 |
| WO | 2014/055944 A1 | 4/2014 |
| WO | 2014/111892 A1 | 7/2014 |
| WO | 2016/009065 A2 | 1/2016 |
| WO | 2016/009066 A1 | 1/2016 |
| WO | 2017/158201 A1 | 9/2017 |

OTHER PUBLICATIONS

Pacifici et al entitled "Cerebrospinal Fluid miRNA Profiled in HIV-Encephalitis" (J. or Cellular Physiology, vol. 228: pp. 1070-1075; published online Oct. 5, 2012). (Year: 2012).*

Enlarged Figure One of Tatro et al in "Evidence for Alteration of Gene Regulatory Networks through MicroRNAs of the HIV-Infected Brain: Novel Analysis of Retrospective Cases" (PLoSone vol. 5, No. 4, e10337, pp. 1-13, published Apr. 20, 2010). (Year: 2010).*

Oct. 10, 2017 Office Action issued in Russian Patent Application No. 2015133373/10(051397).

Maung, et al., "Genetic Knockouts Suggest a Critical Role for HIV Co-Receptors in Models of HIV gp120-Induced Brain Injury," J. Neuroimmune Pharmacol, 7(2): 306-318, Jun. 2012.

Letendre, et al., "The effects of hepatitis C, HIV, and methamphetamine dependence on neuropsychological performance: biological correlates of disease," AIDS 2005, 19 (suppl 3), S72-S78.

Lai, et al., "Micro RNAs are complementary to 3' UTR sequence motifs that mediate negative post-transcriptional regulation", Nature Genetics, vol. 30, No. 4, pp. 363-364, 2002.

Bartel, et al., "MicroRNAs: Target Recognition and Regulatory Functions", Cell, vol. 136, No. 2, pp. 215-233, 2009.

Lindow, et al., "Principles and Limitations of Computational MicroRNA Gene and Target Finding", DNA and Cell Biology, vol. 26, No. 5, pp. 339-351, 2007.

Lee, et al., "MicroRNA maturation: stepwise processing and subcellular localization", EMBO Journal, vol. 21, No. 17, pp. 4663-4670, 2002.

Altuvia, et al., "Clustering and conservation patterns of human microRNAs", Nucleic Acids Research, 2005, vol. 33, No. 8, pp. 2697-2706, 2005.

Ozsolak, et al., "Chromatin structure analyses identify miRNA promoters", Genes and Development, vol. 22, No. 22, pp. 3172-3183, 2008.

Liu, et al., "The evolution and functional diversification of animal microRNA genes", Cell Research, vol. 18, No. 10, pp. 985-996, 2008.

Kim, et al., "Processing of intronic microRNAs", EMBO Journal, vol. 26, No. 3, pp. 775-783, 2007.

Baskerville, et al., "Microarray profiling of microRNAs reveals frequent coexpression with neighboring miRNAs and host genes", RNA, vol. 11, No. 3, pp. 241-247, 2005.

Houzet, et al., "MicroRNAs and human retroviruses," Biochimica et Biophysica Acta, 1809(11-12), pp. 686-693, 2011.

Guo, et al., "Haplotype Distribution and Evolutionary Pattern of miR-17 and miR-124 Families Based on Population Analysis", PLoS ONE, vol. 4, Issue 11, 2009.

Bustin, "Absolute quantification of mRNA using real-time reverse transcription polymerase chain reaction assays", Journal of Molecular Endocrinology, vol. 25, pp. 169-193, 2000.

Klinck, et al., "Multiple Alternative Splicing Markers for Ovarian Cancer", Cancer Research, vol. 68, No. 3, pp. 657-663, 2008.

Nair, et al., "Virus-encoded micro-RNAs: novel regulators of gene expression", TRENDS in Microbiology, vol. 14, No. 4, pp. 169-175, 2006.

Nolan, et al., "Quantification of mRNA using real-time RT-PCR", Nature Protocols, vol. 1, No. 3, pp. 1559-1582, 2006.

Wang, et al., "Quantitation of mRNA by the polymerase chain reaction", Proc. Natl. Acad. Sci., vol. 86, pp. 9717-9721, 1989.

Wong, et al., "Real-time PCR for mRNA quantitation", BioTechniques, vol. 39, No. 1, pp. 75-85, 2005.

Zeng, et al., "Epigenetic regulation of miR-124 by Hepatitis C Virus core protein promotes migration and invasion of intrahepatic cholangiocarcinoma cells by targeting SMYD3", FEBS Letters, vol. 586, No. 19, pp. 3271-3278, 2012.

Witwer, et al., "Relationships of PBMC microRNA expression, plasma viral load, and CD4+ T-cell count in HIV-1-infected elite suppressors and viremic patients", Retrovirology, vol. 9, No. 1, 2012.

Pacifici, et al., "Cerebrospinal fluid miRNA profile in HIV-encephalitis", Journal of Cellular Physiology, vol. 228, No. 5, pp. 1070-1075, 2013.

Apr. 17, 2014 International Search Report issued in International Application No. PCT/IB2014/058359.

Apr. 17, 2014 Written Opinion issued in International Application No. PCT/IB2014/058359.

Aug. 28, 2017 Notice of Reasons for Rejection issued in Japanse Patent Application No. 2015-553212.

Peng et al., MicroRNA-124 Deactivates Human HIV-1-Infected and Classically Activated Macrophages/microglia: Implication for Neurogenesis., J. Neuroimmune Pharmacol (2012), vol. 7, Suppl. 1, pp. S75-S76.

(56) References Cited

OTHER PUBLICATIONS

A.K. El-Damasy et al. "Novel 5-substituted-2-anilinoquinolines with 3-(morpholino or 4-methylpiperazin-1-yl)propoxy moiety as broad spectrum antiproliferative agents: Synthesis, cell based assays and kinase screening." Bioorganic & Medicinal Chemistry Letters, vol. 26, No. 14, May 2016, pp. 3307-3312.

A.L. Wilson et al. "New Trends in Anti-Cancer Therapy: Combining Conventional Chemotherapeutics with Novel Immunomodulators." Current Medicinal Chemistry, vol. 25, No. 36, Dec. 2018, pp. 4758-4784.

J. Zugazagoitia et al. "Current Challenges in Cancer Treatment." Clinical Therapeutics, vol. 38, No. 7, May 2016, pp. 1551-1566.

N.A. Lack et al. "Targeting the Binding Function 3 (BF3) Site of the Human Androgen Receptor through Virtual Screening." Journal of Medicinal Chemistry, vol. 54, No. 24, Dec. 2011, pp. 8563-8573.

Boganyi et al., "Syntheses of New Quinoline-Containing Heterocyclic Scaffolds Using Inter- and Intramolecular Pd-Catalyzed Amination," Journal of Heterocyclic Chemistry, 2009, vol. 46, No. 1, pp. 33-38.

Brandt et al., "Uncoupling activity and physicochemical properties of derivatives of fluazinam," Biochimica et Biophysica Acta, Protein Structure and Molecular Enzymology, 1101(1): 41-7, 1992, abstract only CA 117:82915.

Buchmann et al., "The Preparation and Reactivity of 4-hydroxy-7-chloroquinaldine," Journal fuer Praktische Chemie, 1962, vol. 17, pp. 135-146.

Brune et al., "Progeria: A New Kind of Laminopathy—Clinical and Molecular Update of the Hutchinson-Gilford Syndrome," 1st European Symposium, 2003.

CAPLUS Record for Loriga et al., "Part 7." (Retrieved Nov. 2013).

CAPLUS Record for Loriga et al., "Part 8." (Retrieved Nov. 2013).

Cartegni et al., "Correction of Disease-associated Exon Skipping by Synthetic Exon-specific Activators," Nature Structural Biology, 2003, vol. 10, No. 2, pp. 120-125.

Cartegni et al., "Listening to Silence and Understanding Nonsense: Exonic Mutations that Affect Splicing," Nature Reviews—Genetics, Apr. 2002, vol. 3, pp. 285-298.

Carter et al., "Quinoxalines and related compounds-X-1", Tetrahedron, 34(7), p. 981-988, 1978.

CAS (Chemical Abstracts Service) Registry No. 1011408-51-7, American Chemical Society, added on STN on Apr. 1, 2008, 1 page.

CAS (Chemical Abstracts Service) Registry No. 92873-44-4, American Chemical Society, added on STN on Dec. 7, 1984, 1 page.

CAS (Chemical Abstracts Service) Registry No. 94541-69-2, American Chemical Society, added on STN on Feb. 3, 1985, 1 page.

CAS Registry No. 10562-04-6 added on STN on Nov. 16, 1984.

CAS Registry No. 138386-77-3 added on STN on Jan. 17, 1992.

CAS Registry No. 204851-25-2 added on STN on Apr. 30, 1998.

CAS Registry No. 208661-32-9 added on STN on Jul. 19, 1998.

CAS Registry No. 215589-34-7 added on STN on Dec. 15, 1998.

Hofmann et al., "Htra2-β1 Stimulates an Exonic Splicing Enhancer and can Restore Full-length SMN Expression to Survival Motor Neuron 2 (SMN2)," PNAS, 2000, vol. 97, No. 17, pp. 9618-9623.

Hostyn et al. "Synthesis of ?-Carbolines Starting from 2,3-Dichloropyridines and Substituted Anilines." Advanced Synthesis & Catalysis, Wiley, vol. 350, Oct. 2008, pp. 2653-2660.

J. Tazi et al., "Alternative Splicing and Disease," Biochimica et Biophysica Acta, 1792 (2009), 14-26.

Johnson et al., "Genome-Wide Survey of Human Alternative Pre-mRNA Splicing with Exon Junction Microarrays," Science, vol. 302, pp. 2141-2144, 2003.

Jonckers et al. "Selective Palladium-Catalyzed Aminations of Dicholoropyridines," Tetrahedron, 2001, vol. 57, pp. 7027-7034.

Kaczmarek et al. "Synthesis and Antineoplastic Properties of Some Benzoiso-.Alpha.-Carbolines". Archiv Der Pharmazie, Weinheim, Germany, vol. 321, No. 8, pp. 463-467, 1988.

Katoh et al. "Isolation of the intermediates and improved synthesis of pyrido[1',2':1 ,2]imidazo[4, 5b]pyrazines and -quinoxalines", Heterocycles, 1992, 34(10), p. 1965-1972.

Khalifa. "Hutchinson-Gilford Progeria Syndrome: Report of a Libyan Family and Evidence of Autosomal Recessive Inheritance". Clinical Genetics, vol. 35, pp. 125-132, 1989.

Kondratenko et al. "Bactericidal Activity of Some Derivatives of N-Heteroaromatic Compounds". Mikrobiologichnii Zhumal, 1934-1977, vol. 40, No. 3, pp. 368-370 (abstract only), 1978.

Labourier et al. "Recognition of Exonic Splicing Enhancer Sequences By the *Drosophila* Splicing Repressor RSF1" Nucleic Acids Research, vol. 27, No. 11, pp. 2377-2386, 1999.

Lin Min et al., "Nonsense-mediated mRNA decay and tumors," Journal of International Pathology and Clinical Medicine, vol. 26, No. 4, pp. 291-294, Aug. 2006.

Liu et al. "Partial Correction of Endogenous F508 CFTR in Human Cystic Fibrosis Airway Epithelia by Spliceosome-Mediated RNA Trans-Splicing". Nature Biotechnology, vol. 20, pp. 47-52, 2002.

Lombardino. "Some 3-Arylaminoquinoxaline-2-carboxylic Acids", Journal of Medicinal Chemistry, 9(5), p. 770-771, 1996.

Loones et al. "Examination of the Mechanism of the Intramolecular Amination of N-(3-Bromopyridin-2-yl)Azaheteroarylamines and N-(2-Chloropyridin-3-yl)Azaheteroarylamines: A Pd-Catalyzed Amination and/or a Base-Assisted Nucleophilic; Aromatic Substitution?". Tetrahedron, vol. 63, pp. 3818-3825, 2007.

Loones et al. "Synthesis of Pyrido[2, 1:2,3]Imidazo[4,5-B]Quinoline and Pyrido[1,2:1,2]Imidazo[4,5-B] Quinoline and Their Benzo and Aza Analogs via Tandem Catalysis". Tetrahedron, vol. 63, pp. 3954-3961, 2007.

Loriga et al. "Quinoxaline Chemistry. Part 7. 2-[Aminobenzoates]- and 2-[Aminobenzoylglutamate]-Quinoxalines as Classical Antifolate Agents. Synthesis and Evaluation of In Vitro Anticancer, Anti-HIV and Antifungal Activity". Farmaco, vol. 52, pp. 157-166, (PubMed Abstract No. 9212450), 1997.

Loriga et al. "Quinoxaline Chemistry. Part 8. 2-[Anilino]-3-[Carboxy]-6(7)-Substituted Quinoxalines as Non Classical Antifolate Agents. Synthesis and Evaluation of Invitro Anticancer, Anti-HIV and Antifungal Activity". Farmaco, vol. 52, pp. 531-537, 1997.

Maes et al. "The First Rapid Palladium-Catalyzed Aminations of (Azahetero)aryl Chlorides under Temperature-Controlled Microwave Heating." Synlett, Thieme Medical Publishers, No. 12, Sep. 2003, pp. 1822-1825.

Manley et al. "Sr Proteins and Splicing Control". Genes & Development, vol. 10, pp. 1569-1579,1996.

Molina et al., "C=C-Conjugated Carbodiimides as 2-Azadienes in Intramolecular [4+2] Cycloadditions. One-Pot Preparation of Quinoline, alpha-Cabroline, and Quinindoline Derivatives," J. Org. Chem., 1992, vol. 57, pp. 929-939.

Nguyen et al., "Synthesis and Biological Evaluation of Amino-Substituted Benzo [f]pyrido[4,3-b] and Pyrido [3,4-b] quinoxalines: a New Class of Antineoplastic Agents," Anti-Cancer Drug Design, 1995, vol. 10, No. 4, 277-97.

Nissim-Rafinia et al., "Cellular and Viral Splicing Factors Can Modify the Splicing Pattern of CFTR Transcripts Carrying Splicing Mutations," Human Molecular Genetics, 2000, vol. 9, No. 12, pp. 1771-1778.

Organ et al. "Pd-Catalyzed Aryl Amination Mediated by Well Defined, N-Heterocyclic Carbene (NHC)-Pd Precatalysts, PEPPSI**." Chemistry: A European Journal, Wiley, vol. 14, Feb. 2008, pp. 2443-2452.

Pan et al., "Deep surveying of alternative splicing complexity in the human transcriptome by high-throughput sequencing," Nature Genetics, vol. 40, No. 12, pp. 1413-1415, Dec. 2008.

Park et al. "Efficient Palladium-Catalyzed Amination of Aryl Chlorides Using Dicyclo-Hexylamino[(2,6-Dimethyl)Morpholino]Phenylphosphine as a Pn.Sub.2 Ligand". Synthesis, No. 5, pp. 0815-0823, 2009.

Pauwels. "Aspects of Successful Drug Discovery and Development". Antiviral Res. vol. 71, pp. 77-89, 2006.

Pendas et al. "Defective Prelamin a Processing and Muscular and Adipocyte Alterations in ZMPSTF24 Metalloproteinsase-Deficient Mice". Nature Genetics, vol. 31, pp. 94-99, 2002.

Perry et al. "AIDS dementia: a review of the literature". Alzheimer Dis. Assoc. Disord. 1, pp. 221-235, (PubMed Abstract 3331119), 1987.

(56) References Cited

OTHER PUBLICATIONS

Powell et. al., "Expression, characterisation and mutagensis of the aspartic proteinase from equine infections anaemia virus," European Journal of Biochemistry, 1996, FEBS, vol. 241, pp. 664-674.
Ducrocq et al., "Synthesis of 10-substituted 5H-pyrido[3', 4':4,5]pyrrolo[2,3-]isoquinolines," Journal of the Chemical Society, Perkin Transactions 1: Organic and Bio-Organic Chemistry (1972-1999), 1979, vol. 1, pp. 142-145.
Dudash et al., "Synthesis and Evaluation of 3-anilio-quinoxalinones as glycogen phosphorlyase inhibitors", Bioorganic & Medicinal Chemistry Letters, 15(21), p. 4790-4793, 2005.
Edwards et al., "Orf-I amd Orf-II-Encoded Proteins in HTLV-1 Infection and Persistence", Viruses, 2011, MDPI, vol. 3, pp. 861-885.
El-Sayed et al. "Synthesis of Some Novel Quinoline-3-Carboxylic Acids and Pyrimidoquinoline Derivatives as Potential Antimicrobial Agents". Archiv der Pharmize, vol. 335, No. 9, pp. 403-410, 2002.
Etukala et al., "A Short and Convenient Synthesis and Evaluation of the Antiinfective Properties of Indoloquinoline Alkaloids: 10H-Indolo[3,2-b]quinoline and 7H-Indolo[2,3-c]quinolines," Journal of Heterocyclic Chemistry, No. 45, Mar. 2008, pp. 507-511.
Ewing et al., "Analysis of Expressed Sequence Tags Indicates 35,000 Human Genes," Nature Genetics, 2000, vol. 25, pp. 232-234.
F. J. Leinweber, "Possible Physiological Roles of Carboxylic Ester Hydrolases," Drug Metabolism Reviews, vol. 18, No. 4, pp. 379-439, 1987.
File Registry on STN, 101350-67-8, entered on Apr. 5, 1986.
File Registry on STN, 195876-33-6/RN, entered on Oct. 23, 1997.
File Registry on STN, 408510-56-5, entered on Apr. 29, 2002.
File Registry on STN, 55360-88-8, entered on Nov. 16, 1984.
File Registry on STN, 67412-46-8, entered on Nov. 16, 1984.
File Registry on STN, 70125-24-5/RN, entered on Nov. 16, 1984.
File Registry on STN, 92873-44-4, entered on Dec. 7, 1984.
File Registry on STN, 94541-69-2, entered on Feb. 3, 1985.
File Registry on STN, 97978-62-6, entered on Sep. 16, 1985.
Fong et al., "A Protein Farnesyltransferase Inhibitor Ameliorates Disease in a Mouse Model of Progeria," Science, 2006, vol. 311, pp. 1621-1623.
Fors et al., "An Efficient Process for Pd-Catalyzed C—N Cross-Coupling Reactions of Aryl Iodides: Insight Into Controlling Factors," J. Am Chem. Soc., 2009, 131, 5766-5768.
G. Bhattancharjee et al. "Synthesis of physiologically important quinoxaline derivatives using conventional method and microwave irradiation." Indian Journal of Chemical Technology, Council of Scientific & Industrial Research, vol. 15, No. 1, Jan. 2008, pp. 72-74.
Gordon et al., "Hutchinson-Gilford Progeria Syndrome," NCBI Bookshelf, 2003, accessed Http://www.ncbi.nlm.gov/books/NBK1121/ on Jan. 26, 2016,21 pages.
Graveley, "Sorting out the Complexity of SR Protein Functions," RNA, 2000, vol. 6, pp. 1197-1211.
Gritsenko et al., "Synthesis in Phenothiazines. XXXIX. Dimethylpyridophenothiazines," Khimiya Geterotsiklicheskikh Soedinenii,1975, vol. 1, pp. 50-51.
Grout et al., "Polyazabenzo[a]pyrenes," Journal of the Chemical Society [Section] C: Organic, 1968, vol. 21, pp. 2689-2693.
Hernandez-Lopez et al., "Alternative splicing in human tumour viruses: a therapeutic target?" Biochemical Journal, 2012, Biochemical Society, vol. 445, pp. 145-156.
U.S. Appl. No. 15/552,587, filed Aug. 22, 2017 in the name of Scherrer et al.
U.S. Appl. No. 16/787,471, filed Feb. 11, 2020 in the name of Tazi et al.
U.S. Appl. No. 17/113,369, filed Dec. 7, 2020 in the name of Tazi et al.

Prostakov et al., "Schiff Bases in Syntheses of Substituted Naphthylamines, Napthyridines, Azophenanthrenes, and Benzocarbazole," Khimiya Geterotsiklicheskikh Soedinenii, 1972, vol. 10, pp. 1400-1403.
Rauws et al. "Synthesis of new tetracyclic azaheteroaromatic cores via auto-tandem Pd-catalyzed and one-pot Pd-and Cu-catalyzed double C—N bond formation." Tetrahedron, Elsevier, vol. 66, Jun. 2010. 6958-6964.
Respess et al., "Evaluation of an Ultrasensitive p24 Antigen Assay as a Potential Alternative to Human Immunodeficiency Virus Type 1 RNA Viral Load Assay in Resource-Limited Settings," Journal of Clinical Microbiology, vol. 43, No. 1, pp. 506-508, 2005.
S.D. Carter et al. "Quinoxalines and Related Compounds-X: The Formation of Indolo[2,3-b]Quinoxalines and 2-p-Aminophenyl-3-Anilinoquinoxalines from 2-Anilinoquinoxalines." Tetrahedron, Pergamon Press, vol. 34, Issue No. 7, 1978, pp. 981-988.
Sanchez-Martin et al. "Symmetrical Bis-Quinolinium Compounds: New Human Choline Kinase Inhibitors with Antiproliferative Activity against the HT-29 Cell Line". Journal of Medicinal Chemistry, vol. 48, No. 9, pp. 3354-3363, 2005.
Sazani et al. "Modulation of Alternative Splicing by Antisense Oligonucleotides". Prog. Mol. Subcell. Biol., vol. 31, pp. 217-239, 2003.
Sazani et al. "Systemically Delivered Antisense Oligomers Upregulate Gene Expression in Mouse Tissues". Nature Biotechnology, vol. 20, pp. 1228-1233, 2002.
Schmittel et al. "Two Novel Thermal Biradical Cyclizations in Theory and Experiment: New Synthetic Routes to 6H-Indolo[2,3-b]quinolines and 2-Amino-quinolines from Enyne-Carbodiimides**." Angewandte Chemie International Edition, Wiley, vol. 37, No. 17, Dec. 1998, pp. 2371-2373.
Sharp. "Split Genes and RNA Splicing". Cell, vol. 77, pp. 805-815, 1994.
Silberg et al. "N-Acyl-N, N-Dipyridyl and N-Acyl-N-Pyridyl-N-Quinoyl Amine Based Palladium Complexes. Synthesis, X-Ray Structures, Heterogenization and Use in Heck Couplings". Journal of Organmetallic Chemistry, vol. 622, pp. 6-18, 2001.
Solekhova et al. "Reductive Amination of Quinoline N-Oxide With Aminopyridines and Their N-Tosyl Derivatives" Russian Journal of Organic Chemistry, vol. 38, No. 8, pp. 1192-1194, 2002.
STN Database Registration No. 374598-11-5, Chemical Abstracts Service, American Chemical Society, Registered Oct. 1, 2007, pp. 1-10.
STN Database Registration No. 397881-66-2, Chemical Abstracts Service, American Chemical Society, Registered Mar. 4, 2002, 1 page.
STN Database Registration No. 933238-11-0, Chemical Abstracts Service, American Chemical Society, Registered Apr. 29, 2007, pp. 1-4.
Talik et al., "2-Chloro-3, 5-dinitropyridine. 1. Exchange Reactions of the Chlorine Atom," Bulletin de L'Academie Polonaise des Sciences, Serie Des Sciences Chimiques, 1960, vol. 8, No. 5, pp. 219-222.
Tazi et al. "A Protein That Specifically Recognizes The 3' Splice Site of Mammalian Pre-MRNA Introns is Associated With a Small Nuclear Ribonucleoprotein" Cell, vol. 47, pp. 755-766, 1986.
Tazi et al. "The Spliceosome: a Novel Multi-Faceted Target for Therapy". Trends in Biochemical Sciences, vol. 30, No. 8, pp. 469-478, 2005.
Varela et al., "Combined Treatment with Statins and Aminobisphosphonates Extends Longevity in a Mouse Model of Human Premature Aging," Nature Medicine, 2008, vol. 14, No. 7, pp. 767-772.
Vulliamy et al., "Mutations in the Telomerase Component NHP2 Cause the Premature Ageing Syndrome Dyskeratosis Congenita," PNAS, 2008, vol. 105, No. 23, pp. 8073-8078.
Walker et al., "Rheumatic conditions in human immunodeficiency virus infection," (Rheumatology 2008;47:952-959). (Year: 2008).
Wang et al. "A Direct Intramolecular C—H Amination Reaction Cocatalyzed by Copper (II) and Iron (III) as Part of an Efficient Route for the Synthesis of Pyrido[1,2-a]benzimidazoles from N-Aryl-2-aminopyridines." Journal of the American Chemical Society, ACS Publications, vol. 132, Sep. 2010, pp. 13217-13219.

(56) References Cited

OTHER PUBLICATIONS

Wang et al. "Alternative Isoform Regulation in Human Tissue Transcriptomes". Nature, vol. 456, pp. 470-476, 2008.
Wang et al. "SC35 Plays a Role in T Cell Development and Alternative Splicing of CD45". Molecular Cell, vol. 7, pp. 331-342, 2001.
Yanborisova et al., "Synthesis and Antiinflammatory Activity of 2-Arylaminocinchoninic Acids and Amides of 1,2-Dihydro-2-Oxocinchoninic Acid," Pharmaceutical Chemistry Journal, vol. 29, No. 6, Jun. 1995, pp. 404-405.
Rolak, Clin Med Res, Jan. 2003, vol. 1 (1), 57-60, 2003.
U.S. Appl. No. 13/993,990, filed Jun. 13, 2013 in the name of Tazi et al.
CAS Registry No. 294668-01-2 added on STN on Oct. 11, 2000.
CAS Registry No. 313266-85-2 added on STN on Jan. 9, 2001.
CAS Registry No. 324526-73-0 added on STN on Feb. 27, 2001.
CAS Registry No. 342653-87-6 added on STN on Jun. 20, 2001.
CAS Registry No. 449780-94-3 added on STN on Sep. 12, 2002.
CAS Registry No. 449780-95-4 added on STN on Sep. 12, 2002.
CAS Registry No. 5468-85-9 added on STN on Nov. 16, 1984.
CAS Registry No. 70682-97-2 added on STN on Nov. 16, 1984.
CAS Registry No. 1004363-48-7 added on STN on Feb. 19, 2008.
CAS Registry No. 1011408-51-7 added on STN on Apr. 1, 2008.
CAS Registry No. 1135230-99-7 added on STN on Apr. 16, 2009.
CAS Registry No. 330663-16-6 added on STN on Apr. 10, 2001.
CAS Registry No. 374598-11-5 added on STN on Dec. 10, 2001.
CAS Registry No. 438481-24-4 added on STN on Jul. 12, 2002.
Connor et al., "Vpr is Required for Efficient Replication of Human Immunodeficiency Virus type-1 in Mononuclear Phagocytes," Virology, 1995, vol. 206, pp. 935-944.
Cottet et al., "Recommendable Routes to Trifluoromethyl-Substituted Pyridine-and Quinolinecarboxylic Acids," Eur. J. Org. Chem., 2003, pp. 1559-1568.
De Sandre-Giovannoli et al. "Lamin a Truncation in Hutchinson-Gilford Progeria". Science, vol. 300, p. 2055, 2003.
De Sandre-Giovannoli et al., "Altered Splicing in Prelamin A-associated Premature Aging Phenotypes," Progress in Molecular and Subcellular Biology, 2006, pp. 199-232.
Desai et al., "2-Methyl-4-quinoline-hydrazide Derivatives as Antitubercular/Antibacterial Agents—Part I," Asian Journal of Chemistry, vol. 10, No. 2, (1998), pp. 370-372.
Desai et al., "Some Quinoline, Quinazoline and Pyrazine Derivatives as Antitubercular-Antibacterial Agents," Asian Journal of Chemistry, vol. 10, No. 4 (1998), pp. 993-994.
Deuerleine, "Dipryridyl-, diquinolyl-, and Pyridylquinolylamines," Journal fuer Praktische Chemie (Liepzig), 1923, vol. 106, pp. 53-65.
Dhanabal et al., "Heteroatom Directed Photoannulation: Synthesis of Indoloquinoline Alkaloids: Cryptolepine, Cryptotackieine, Cryptosanguinolentine, and their Methyl Derivatives," Tetrahedron, 2006, vol. 62, pp. 6258-6263.
Dignam et al., "Eukaryotic Gene Transcription with Purified Components," Methods in Enzymology, 1983, vol. 101, pp. 582-598.
Dobson, J. et al., "Attempts to find new antimalarials. XXVII. Derivatives of various benzacridines and pyridoacridines", Journal of the Chemical Society, pp. 123-126, Jan. 1948.

\* cited by examiner

MIRNA-124 AS A BIOMARKER

The present application contains a Sequence Listing that has been submitted electronically in ASCII format and is hereby incorporated by reference in its entirety. The ASCII copy, created on Mar. 29, 2018, is named 5545435_1.TXT and is 16,138 bytes in size.

The instant invention relates to the field of biomarkers, in particular in connection with viral infections.

More particularly, the invention relates to a novel biomarker useful as a diagnostic marker for viral infections. The viral infections more particularly considered are viral infections requiring RNA splicing, and in particular retroviral infections such as HIV and AIDS-related conditions. The invention also relates to a follow-up marker for treatments of said infections, and in particular HIV and AIDS-related conditions.

In higher eukaryotes, messenger RNAs are not directly transcribed in their functional form but as pre-messenger RNAs which have to go through many processing events in order to be readable by the cellular translation machinery. Splicing is the process which allows to eliminate the unwanted sequences (introns) and to join the meaningful ones (exons). The highly coordinated splicing event takes place in a large complex called the Spliceosome. The formation of this functional megacomplex is an orchestrated assembly of proteins and RNA that requires identification of exon-intron boundaries. Exons are regularly alternatively spliced, meaning that they are either included or excluded from the final mature mRNA transcript. A recent comprehensive sequencing study observed that more than 90% of the genes undergo alternative splicing. The production of alternatively spliced mRNAs is regulated by a system of trans-acting proteins that bind to cis-acting sites on the pre-mRNA itself. Such proteins include splicing activators that promote the usage of a particular splice site, and splicing repressors that reduce the usage of a particular site, binding on splicing enhancer sites (intronic splicing enhancers, ISE and exonic splicing enhancers, ESE) and on splicing silencer sites (intronic splicing silencers, ISS and exonic splicing silencers, ISS) respectively.

Viruses, in particular from the retroviral family, are one of the major causes of diseases around the world. Three subfamilies can be distinguished within the retroviral family: the oncoviruses, the lentiviruses and the spumaviruses.

The oncoviruses are thus termed because they can be associated with cancers and malignant infections. There may be mentioned, for example, leukemogenic viruses (such as the avian leukemia virus (ALV), the murine leukemia virus (MULV), also called Moloney virus, the feline leukemia virus (FELV), human leukemia viruses such as HTLV1 and HTLV2, the simian leukemia virus or STLV, the bovine leukemia virus or BLV, the primate type D oncoviruses, the type B oncoviruses which are inducers of mammary tumors, or oncoviruses which cause a rapid cancer (such as the Rous sarcoma virus or RSV).

The spumaviruses manifest fairly low specificity for a given cell type or a given species, and they are sometimes associated with immunosuppressive phenomena; that is the case, for example, for the simian foamy virus (or SFV).

The lentiviruses, such as HIV, are thus named because they are responsible for slow-progressing pathological conditions which very frequently involve immunosuppressive phenomena, including AIDS.

Viruses, and in particular retroviruses such as HIV, are known to rely upon RNA splicing and splicing regulation in order to spread and disseminate within cells and tissues of an infected individual.

Recently, the fact that HIV is a retrovirus that requires RNA splicing to express key viral proteins has been exploited to develop a novel strategy based on splicing inhibition to combat viral infections, and in particular AIDS (WO 2010/143169). Indeed, the HIV-1 genome expresses a primary transcript of 9 kb that not only serves as a genomic RNA for progeny virus, but which also generates 40 different mRNAs. HIV-1 uses four multiple alternative 5' splice sites and eight multiple alternative 3' splice sites to generate spliced mRNA species. These spliced mRNAs can be divided into two classes: multiply spliced (2 kb) and singly spliced (4 kb) RNAs. Regulation of HIV-1 alternative splicing occurs primarily because of the presence of suboptimal splicing sites which decrease the recognition by the cellular splicing machinery of the splice signals. Splicing at the viral splice sites is further regulated by the presence of ESEs, ESSs and ISSs.

In this context, quinoline derivatives have been developed, in particular 8-chloro-N-[4-(trifluoromethoxy)phenyl]quinolin-2-amine, which has been shown to inhibit replication in Peripheral Blood Mononuclear Cells (PBMC) of HIV-1 and HIV-2 T cell-tropic laboratory strains as well as clinical isolates of different subtypes at nM concentrations range (WO 2010/143169).

microRNAs (miRNA), the most comprehensive noncoding group, are a class of about 22 nt noncoding RNAs that inhibit gene expression through binding to the UnTranslated Region (UTR) of target mRNA transcripts (Lai et al., Nature Genetics, vol. 30, no. 4, pp. 363-364, 2002; Bartel et al., Cell, vol. 136, no. 2, pp. 215-233, 2009). miRNA genes represent about 1-2% of the known eukaryotic genomes. Predictions suggest that each miRNA can target more than 200 transcripts and that a single mRNA can be regulated by multiple miRNAs (LINDOW, DNA Cell Biol., vol. 26(5), p. 339-351, 2007). miRNAs are generated from endogenous hairpin-shaped transcripts and act by base pairing with target mRNAs, which leads to mRNA cleavage or translational repression, depending on the degree of base-pairing. Two processing events lead to mature miRNA formation: first, the nascent miRNA transcripts (pri-miRNA) are processed into 70 nucleotides precursors (pre-miRNA) which are exported from the nucleus and are cleaved in the cytoplasm to generate short (about 22 nucleotides long) mature miRNAs (LEE, EMBO J., vol. 21, p; 4663-4670, 2002). miRNAs can be located inter- or intragenically. When intergenic, their expression is coordinated with other miRNAs as a cluster (Altuvia et al., Nucleic Acids Research, vol. 33, no. 8, pp. 2697-2706, 2005, Ozsolak et al., Genes and Development, vol. 22, no. 22, pp. 3172-3183, 2008). When intragenic, namely, positioned within a protein-coding gene (almost exclusively in introns), they are often expressed from the same strand as their host-gene (Liu et al., Cell Research, vol. 18, no. 10, pp. 985-996, 2008, Kim et al, EMBO Journal, vol. 26, no. 3, pp. 775-783, 2007) and at correlated levels (Baskerville et al., RNA, vol. 11, no. 3, pp. 241-247, 2005).

miRNAs have recently been implicated in the intricate cross-talk between the host and the pathogen in viral infections and is thought to play a major role in viral pathogenesis (NAIR, Trends in Microbiol., vol. 14, p. 169-175, 2006). Indeed, viruses are obligate intracellular parasites using the cellular machinery for their survival and replication, so this dependence makes them susceptible to the host gene-regulatory mechanisms. Cellular miRNA can take part in an antiviral defense mechanism, but can, in some cases, also be viral positive regulators. On the other hand, viruses themselves can also produce miRNAs to regulate cellular processes or viral genes. miRNAs involved in HIV-1 infection could be defined as HIV-1-encoded or host-encoded according to their source of biogenesis; they could also be defined as suppressors or activators of infection according to their function. They can be further divided according to whether they directly target HIV-1 transcripts or indirectly affect HIV-1 by targeting host factors that are involved in virus life cycle, or targeting both the HIV-1 RNA genome and host factors essential for HIV-1 infection. Several data attest that HIV-1 infection affects miRNA pathways globally due to miRNA biogenesis perturbation but also individually by miRNA expression profiles modification (Houzet et al., Biochim Biophys Acta. 2011 November-December; 1809 (11-12): 686-693)). Furthermore, host miRNAs have been described to regulate HIV-1.

One key factor for the success of development of a given drug or vaccine is the possibility to assess efficiently and rapidly its efficacy. Indeed, it is important for a given drug or vaccine to be administered in its therapeutic window so as to avoid unwanted effects coming from a too high dosage or to avoid a lack of efficiency due to a too low dosage. Also, one has to be sure that the proper drug or vaccine is administered to the proper patient, and that this patient is indeed responsive to the drug or vaccine. Therefore, simply linking together a given patient and a given drug or vaccine is not always enough to obtain a beneficial therapeutic effect. It is therefore critical to have proper tools, such as specific biomarkers, to rely upon for assessing the efficacy of a drug or vaccine.

Therefore, there is a need for a novel and sensitive tool for assessing a viral infection, and in particular a retroviral infection, and more particularly an HIV (Human Immunodeficiency Virus) infection, as well as the efficacy of a treatment of such conditions.

There is need for a novel biomarker for assessing the efficacy of a treatment of a viral infection, and in particular a retroviral infection, and more particularly an HIV infection.

There is a need for a novel and sensitive tool for assessing the efficiency of quinoline derivatives which are inhibitors of viruses, in particular retroviruses such as HIV, and more particularly HIV-1 and HIV-2.

There is a need for a novel biomarker for assessing the responsiveness of a patient to quinoline derivatives for preventing or treating a viral infection, and in particular a retroviral infection, and more particularly an HIV infection.

There is a need for a novel biomarker for assessing the therapeutic efficacy of quinoline derivatives for preventing or treating a viral infection, and in particular a retroviral infection, and more particularly an HIV infection.

There is also a need for a novel biomarker for screening drug candidates or vaccine effective for preventing and/or treating a viral infection, and in particular a retroviral infection, and more particularly an HIV infection.

The present invention has for purpose to meet these needs.

According to one of its objects, the invention concerns a use of at least one miRNA, said at least one miRNA being miR-124, as a biomarker of a viral infection, or of an efficacy of a therapeutic treatment of said viral infection.

Unexpectedly, the inventors have observed, as detailed in the examples below, that, in PBMCs infected with an HIV strain, in particular with an ADA-M R5 HIV strain, the level of expression of miR-124 was decreased relative to non-infected PBMCs.

What is more, the inventors have unexpectedly observed that a treatment with quinoline derivatives, such as quinoline derivatives of formula (I) or (II), and in particular with the 8-chloro-N-[4-(trifluoromethoxy)phenyl]quinolin-2-amine, of peripheral blood mononuclear cells (PBMCs) infected with a HIV strain, in particular with the ADA-M R5 HIV, resulted in the removal of the viruses and in a dramatic increase (13-fold relative to control) of miR-124 expression.

Quinoline derivatives may be chosen among the compounds described in WO 2010/143169 and as further described below. Accordingly, a therapeutic treatment of said viral infection can be a treatment with quinoline derivatives.

Accordingly, the miR-124 revealed itself as power tool, otherwise said as a biomarker, for monitoring a viral infection, in particular a retroviral infection, such as an HIV infection, in particular into individuals suffering from such an infection, as well as for monitoring individuals infected with a virus, in particular a retrovirus, such as an infection with HIV, and for monitoring such individuals treated with an antiviral drug, in particular with quinoline derivatives of formula (I) or (II) as detailed below, and in particular with 8-chloro-N-[4-(trifluoromethoxy)phenyl]quinolin-2-amine.

Thus, by monitoring the level of expression of miR-124, it is possible to track or perform quality control on human research trials or to monitor the patient compliance to a drug regimen or vaccine by providing a means to confirm that the patient is receiving appropriate drug or vaccine treatments, i.e., in terms of the dose and time. The miR-124 biomarker can also be used to optimize dosing regimens. Thus, miR-124 biomarker can be used in connection with, for example, the management of patient treatment, clinical trials, and cell-based research.

According to another of its objects, the invention concerns a use of at least one miRNA, said at least one miRNA being miR-124, as a biomarker of a viral infection, preferably with a retrovirus, and more preferably with a Human Immunodeficiency Virus (HIV).

According to another of its objects, the invention pertains a use of at least one miRNA, said at least one miRNA being miR-124, as a biomarker for screening a drug candidate or vaccine candidate presumed effective in preventing and/or treating a viral infection, in particular a retroviral infection, and more particularly an HIV infection.

According to another of its objects, the invention concerns the use of at least one miRNA, said at least one miRNA being mi RNA-124, as a biomarker, for assessing the biological effect, in particular the pharmacological potential, of a candidate compound, to alter the physiological activity of a cell or a protein.

In this respect, it has been shown herein that the level of expression of miR-124 varies upon administration of various compounds that are known to possess a pharmacological activity. Thus, the inventors have shown that miR-124 consists of a relevant biomarker of the potential pharmacological activity of a candidate compound.

In particular, the drug candidate or vaccine candidate presumed effective in preventing and/or treating a viral infection can be a quinoline derivative.

In particular, the drug candidate or vaccine candidate presumed effective in preventing and/or treating a viral infection can be a quinoline derivative of formula (I):

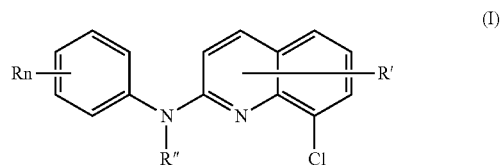

(I)

wherein n is 1 or 2 and R, independently, represents a hydrogen atom, a halogen atom or a group chosen among a $(C_1-C_3)$alkyl group; a $-NR_1R_2$ group in which $R_1$ and $R_2$ are independently a hydrogen atom or a ($C_1$-$C_3$) alkyl group; a ($C_1$-$C_3$) fluoroalkoxy group; a —$NO_2$ group; a phenoxy group; and a ($C_1$-$C_4$) alkoxy group, R' is a hydrogen atom, a halogen atom or a group chosen among a ($C_1$-$C_4$) alkyl group and a ($C_1$-$C_4$) alkoxy group, R" is a hydrogen atom or a ($C_1$-$C_4$) alkyl group, or one of its pharmaceutically acceptable salt.

The drug candidate or vaccine candidate presumed effective in preventing and/or treating a viral infection can also be a quinoline derivative of formula (II):

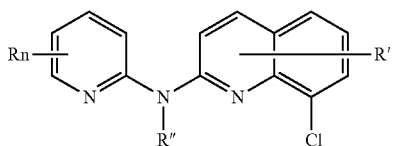

(II)

wherein:
n is 1 or 2 and R, independently, represents a hydrogen atom, a halogen atom or a group chosen among a ($C_1$-$C_3$) alkyl group; a —CN group; a hydroxyl group; a —$COOR_1$ group; a ($C_1$-$C_3$)fluoroalkyl group; a —$NO_2$ group; a —$NR_1R_2$ group with $R_1$ and $R_2$ being a hydrogen atom or a ($C_1$-$C_3$)alkyl group; and a ($C_1$-$C_4$) alkoxy group, R' is a hydrogen atom, a halogen atom or a group chosen among a ($C_1$-$C_4$) alkyl group and a ($C_1$-$C_4$) alkoxy group, R" is a hydrogen atom or a ($C_1$-$C_4$) alkyl group, or one of its pharmaceutically acceptable salt.

Within the invention, the term "preventing" intends to mean reducing the likelihood of occurrence of a given event, namely, in the context of the invention, a viral infection.

According to another of its objects, the invention concerns a use of at least one miRNA, said at least one miRNA being miR-124, as a biomarker of an activity of a quinoline derivative, or one of its pharmaceutically acceptable salt, on a viral infection, in particular a retroviral infection, and more particularly an HIV infection.

According to another of its objects, the invention concerns a use of at least one miRNA, said at least one miRNA being miR-124, as a biomarker of an activity of a quinoline derivative of formula (I):

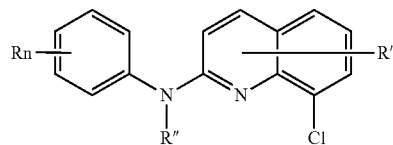

(I)

wherein
n is 1 or 2 and R, independently, represents a hydrogen atom, a halogen atom or a group chosen among a ($C_1$-$C_3$) alkyl group; a —$NR_1R_2$ group in which $R_1$ and $R_2$ are independently a hydrogen atom or a ($C_1$-$C_3$) alkyl group; a ($C_1$-$C_3$) fluoroalkoxy group; a —$NO_2$ group; a phenoxy group; and a ($C_1$-$C_4$) alkoxy group, R' is a hydrogen atom, a halogen atom or a group chosen among a ($C_1$-$C_4$) alkyl group and a ($C_1$-$C_4$) alkoxy group, R" is a hydrogen atom or a ($C_1$-$C_4$) alkyl group, or one of its pharmaceutically acceptable salt, on a viral infection, and in particular a retroviral infection, and more particularly an HIV infection.

According to another of its objects, the invention concerns a use of at least one miRNA, said at least one miRNA being miR-124, as a biomarker of an activity of a quinoline derivative of formula (II):

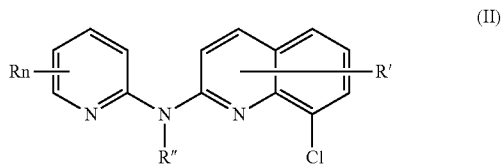

(II)

wherein
n is 1 or 2 and R, independently, represents a hydrogen atom, a halogen atom or a group chosen among a ($C_1$-$C_3$)alkyl group; a —CN group; a hydroxyl group; a —$COOR_1$ group; a ($C_1$-$C_3$)fluoroalkyl group; a —$NO_2$ group; a —$NR_1R_2$ group with $R_1$ and $R_2$ being a hydrogen atom or a ($C_1$-$C_3$)alkyl group; and a ($C_1$-$C_4$) alkoxy group, R' is a hydrogen atom, a halogen atom or a group chosen among a ($C_1$-$C_4$) alkyl group and a ($C_1$-$C_4$) alkoxy group, R" is a hydrogen atom or a ($C_1$-$C_4$) alkyl group, or one of its pharmaceutically acceptable salt, on a viral infection, in particular a retroviral infection, and more particularly an HIV infection.

According to a particular embodiment, a quinoline derivative of the invention may be 8-chloro-N-[4-(trifluoromethoxy)phenyl]quinolin-2-amine or 8-chloro-N-[4-(trifluoromethyl)pyridin-2-yl]quinolin-2-amine.

Thus, according to another of its objects, the invention concerns a use of at least one miRNA, said at least one miRNA being miR-124, as a biomarker of an activity of a quinoline derivative selected from:

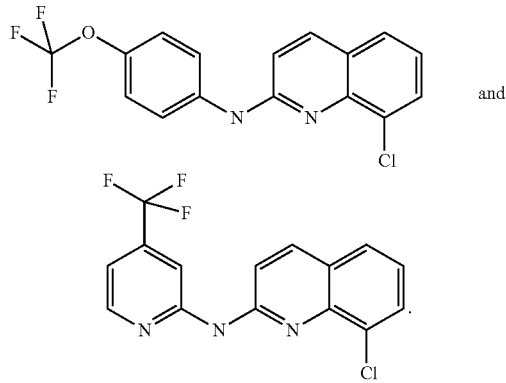

and

Within the invention, the expressions "viral infection" and "infection with a virus" refer to any viral infection, and in particular to any retroviral infection, which may occur into a cell, a tissue, an organ or an individual liable to express a biomarker of the invention. Preferably, a retroviral viral infection may be a lentiviral infection, and more preferably an HIV infection. An individual within the invention may be a mammal, and preferably a human liable to express a biomarker of the invention. Within the invention, individual and patient are used interchangeably.

Within the invention, the term "virus" refers to any virus, in particular a retrovirus and preferably a lentivirus such as an HIV virus, more preferably HIV-1 or HIV-2.

According to another of its objects, the invention pertains to a method for assessing a viral infection, and in particular a retroviral infection, and more particularly an HIV infection, in a patient presumed to be infected with a virus, comprising at least the steps of:

a—measuring a presence or an expression level of at least one miRNA, said at least one miRNA being miR-124, in a biological sample previously obtained from said patient; and b—comparing said presence or expression level to a control reference value, wherein a modulated presence or level of expression of said miRNA relative to said control reference value is indicative of a viral infection.

According to another of its objects, the invention pertains to a method of assessing an activity of a quinoline derivative of formula (I) for preventing and/or treating a viral infection, in particular a retroviral infection, and more particularly an HIV infection, in a patient treated with said quinoline derivative, comprising at least the steps of:

a—measuring a presence or an expression level of at least one miRNA, said at least one miRNA being miR-124, in a first biological sample previously obtained from said patient before administering said quinoline derivative and in a second biological sample previously obtained from said patient after administering said quinoline derivative; and b—determining if said presence or expression level is modulated in the second biological sample obtained after the treatment as compared to the second biological sample obtained before the treatment;

wherein a modulated presence or level of expression of said miRNA is indicative of an activity of said quinoline derivative.

"Biological sample," as used herein, generally refers to a sample obtained from a biological subject, including sample of biological tissue or fluid origin, obtained, reached, or collected in vivo or in situ. Such samples can be, but are not limited to, organs, tissues, fractions and cells isolated from a mammal. Exemplary biological samples include but are not limited to cell lysate, a cell culture, a cell line, a tissue, oral tissue, gastrointestinal tissue, an organ, an organelle, a biological fluid, a blood sample, a serum sample, a urine sample, a skin sample, and the like. Preferred biological samples include but are not limited to a blood, a plasma, a serum, a PBMC, a tissue biopsy, an oral mucosa, a saliva, an interstitial fluid, or an urine sample, and the like.

In one embodiment, a biological sample suitable for the invention may be selected in a group consisting of a biological tissue sample, a whole blood sample, a swab sample, a plasma sample, a serum sample, a saliva sample, a vaginal fluid sample, a sperm sample, a pharyngeal fluid sample, a bronchial fluid sample, a fecal fluid sample, a cerebrospinal fluid sample, a lacrymal fluid sample and a tissue culture supernatant sample.

The invention further relates to an isolated biological sample comprising a biomarker, wherein said biological sample is selected in a group comprising, and preferably consisting in a tissue sample, whole blood, swab sample, plasma, serum, saliva, vaginal fluid, sperm, pharyngeal fluid, bronchial fluid, fecal fluid, cerebrospinal fluid, lacrymal fluid and tissue culture supernatant; wherein said biomarker is a miRNA biomarker, and preferably miR-124.

According to another of its objects, the invention concerns a method for assessing the biological effect of a candidate compound and in particular for screening a drug candidate or vaccine candidate, presumed effective in preventing and/or treating a viral infection, and in particular a retroviral infection, and more particularly an HIV infection, comprising at least the steps of:

a—treating at least one isolated cell able to express at least one miRNA, said at least one miRNA being miR-124, with said candidate, said cell being under conditions suitable for expressing said at least one miRNA, b—measuring a presence or expression level of said at least one miRNA, c—comparing said measured presence or expression level with a measure or expression level of said at least one miRNA in an untreated isolated cell, wherein a modulated presence or level of expression of said miRNA is indicative of a biological effect of a candidate compound and in particular of the efficacy of said drug candidate or vaccine candidate on a viral infection.

Within the invention, the terms "modulation" or "modulated presence or level of expression" intend to mean that the presence or level of expression of a biomarker of the invention is either induced or increased, or alternatively is suppressed or decreased.

Thus, it flows from the experimental results contained herein that miR-124, and notably the expression level of miR-124, consists of a relevant biomarker that is indicative of a physiological change of a protein or a cell, including a metabolic change of a cell, which change materializes a beneficial pharmacological effect.

Then, as stated previously, the invention also concerns the use of at least one miRNA, said at least one miRNA being miRNA-124, for assessing the biological effect, in particular the pharmacological effect, of a candidate compound.

This invention also relates to the use of at least one miRNA, said at least one miRNA being miRNA-124, for assessing the ability of a candidate compound to alter the physiological activity of a protein or a cell.

The alteration of the physiological activity of a protein or a cell may be easily determined by the one skilled in the art by identification of any detectable change in the measure of a physiological parameter of a cell, including in the measure of a metabolic parameter of cell, which encompasses electrophysiological changes, cell membrane permeability changes, enzyme activity changes, protein expression changes, miRNA expression changes, gene expression changes, intracellular pH values, etc.

The terms "determining," "measuring," "evaluating," "assessing," and "assaying," as used herein, generally refer to any form of measurement, and include determining if an element is present or not. These terms include both quantitative and/or qualitative determinations. Assessing may be relative or absolute. The phrase "assessing the presence of" can include determining the amount of something present, as well as determining whether it is present or absent.

According to one preferred embodiment, when assessing a viral infection, an observation of a reduced or suppressed presence, or a decreased level of expression, of said miRNA relative to a control reference value may be indicative of a viral infection.

According to one preferred embodiment, when assessing an activity of a quinoline derivative of formula (I) for treatment of a viral infection or when screening a drug candidate or vaccine candidate presumed effective in preventing and/or treating a viral infection, an observation of an induced or increased presence, or an increased level of expression, of said miRNA relative to a control reference value may be indicative of an activity of said quinoline derivative of formula (I) or of an efficacy of said drug candidate or vaccine candidate.

According to a preferred embodiment, uses and methods of the invention are carried out in vitro or ex vivo.

According to another of its objects, the invention relates to an isolated nucleic acid probe able to specifically hybridize to miR-124 as a diagnostic agent for measuring a presence or a level expression of miR-124 for diagnosing a viral infection, in particular a retroviral infection, and more particularly an HIV infection, or for assessing an activity of a drug candidate or vaccine candidate presumed effective for preventing and/or treating a viral infection, in particular a retroviral infection, and more particularly an HIV infection.

The term "probe" as used herein, generally refers to a capture agent that is directed to a specific target miRNA biomarker sequence. Accordingly, each probe of a probe set has a respective target miRNA biomarker. A probe/target miRNA duplex is a structure formed by hybridizing a probe to its target miRNA biomarker.

An isolated nucleic acid probe suitable for the invention may be preferably a nucleic acid probe consisting in a nucleic acid sequence selected from the group consisting of SEQ ID NO: 6 to SEQ ID NO: 87.

According to one of its advantages, the invention provides a useful and reliable biomarker for the follow-up of patients infected with a virus, preferably with a retrovirus, and more preferably with an HIV virus.

According to one of its advantages, the invention provides a useful and reliable biomarker for the follow-up of patients infected with a virus, preferably with a retrovirus, and more preferably with an HIV virus, and treated with quinoline derivative of formula (I).

According to another of its advantages, the invention provides a sensible and dependable biomarker which may be easily used at the bed of a patient.

Uses and Methods

According to one embodiment, use and methods according to the invention may, in particular, allow for the determining of a viral infection in a patient, and in particular for the follow-up of such infection.

According to one embodiment, a presence or a level of expression of miR-124 is measured into an isolated biological sample, and then is compared to a control reference value.

A modulation of the presence or level of expression of miR-124 relative to the control reference value may be indicative of a viral infection. In particular a reduced or suppressed presence, or a decreased level of expression, of said miRNA relative to a control reference value may be indicative of a viral infection.

In one embodiment, a use of the invention may comprise obtaining of a measured level of expression of said miR-124 into an isolated biological sample and comparing said measured level of expression to a control reference value. An observation of a modulation of said measured level relative to said control reference value may be indicative of a viral infection, or of an efficacy of a therapeutic treatment of said viral infection.

When miR-124 from a sample is "decreased" or "downregulated" in a biological sample isolated from a patient, as compared to a control reference value, this decrease can be, for example, of about 5%, 10%, 20%, 30%, 40%, 50%, 60%, 70%, 90%, 100%, 200%, 300%, 500%, 1,000%, 5,000% or more of the comparative control reference value (i.e., without the treatment by the quinoline derivative).

In particular, the measured level expression of miR-124 may be at least a two-fold, preferably at least a four-fold, preferably at least a six-fold, preferably at least an eight-fold, and more preferably at least a ten-fold decrease relative to said control reference value.

According to one embodiment, uses of and methods implementing miR-124 as a biomarker for a viral infection, and in particular a retroviral infection, and more particularly an HIV infection, may be combined with the determination of others biomarkers specific from said infection such as the determination of the presence or level of expression of peptides, proteins or nucleic acid sequences specific from said virus. Others biomarkers specific from a viral infection, and in particular a retroviral infection, and more particularly an HIV infection, may be, for example, the proteins or the nucleic acid sequences encoding Tat, gp120 or gp41, or a level $T_4$ lymphocytes.

The miR-124 biomarker may be used to monitor or manage a patient suffering from a viral infection, and in particular a retroviral infection, and more particularly an HIV infection or AIDS (Acquired Immune Deficiency Syndrome).

According to one embodiment, the increase of the presence or level of expression of miR-124 in a biological sample taken from a patient suffering from a viral infection and receiving a treatment for this infection relative to a biological sample taken from the same patient before initiating said treatment may be indicative of the efficacy of said treatment.

According to one embodiment, the uses and methods of the invention may be for assessing a responsiveness of a patient to a treatment with said quinoline derivatives of formula (I).

According to another embodiment, the uses and methods of the invention may be for assessing an effectiveness of a treatment with said quinoline derivative of formula (I).

According to another embodiment, the uses and methods of the invention may be for assessing a therapeutic efficacy of quinoline derivatives of formula (I) as a therapeutic agent for preventing and/or treating a viral infection.

According to one embodiment, the uses and methods of the invention may be for assessing a patient compliance with a treatment with said quinoline derivative of formula (I).

The miR-124 biomarker may be used to monitor or manage quinoline derivatives of formula (I) activity during patient treatment of a viral infection, and in particular a retroviral infection, and more particularly an HIV infection or AIDS (Acquired Immune Deficiency Syndrome).

A method of assessing or monitoring the activity of a quinoline derivative of formula (I) in a patient treated with the quinoline derivative may involve measuring a level of expression of miR-124 in an isolated sample, preferably isolated PBMC (Peripheral Blood Mononuclear Cell), and comparing the measured level of expression to a level of expression of miR-124 in an isolated an isolated sample taken from the patient prior to the treatment. By following the miR-124 level, the activity of the quinoline derivative can be monitored over time.

According to one embodiment, a use or a method according to the invention may be implemented for optimizing the dosing regimen of a patient. Patients may respond differently to a given quinoline derivative of formula (I), depending on such factors as age, health, genetic background, presence of other complications, disease progression, and the co-administration of other drugs. It may be useful to utilize the miR-124 biomarker to assess and optimize the dosage regimen, such as the dose amount and/or the dose schedule, of a quinoline derivative in a patient. In this regard, miR-124-based biomarker can also be used to track and adjust individual patient treatment effectiveness over time. The biomarker can be used to gather information needed to make adjustments in a patient's treatment, increasing or decreasing the dose of an agent as needed. For example, a patient receiving a quinoline derivative can be tested using the miR-124-based biomarker to see if the dosage is becoming effective, or if a more aggressive treatment plan needs to be put into place. The amount of administered drug, the timing of administration, the administration frequency, the duration of the administration may be then adjusted depending on the miR-124 biomarker measurement.

The miR-124 biomarker may also be used to track patient compliance during individual treatment regimes, or during clinical trials. This can be followed at set intervals to ensure that the patients included in the trial are taking the drugs as instructed. Furthermore, a patient receiving a quinoline derivative can be tested using the miR-124 biomarker to determine whether the patient complies with the dosing regimen of the treatment plan. An increased expression level of the biomarker compared to that of an untreated control sample is indicative of compliance with the protocol.

A biomarker of the invention may be implemented to assess and follow the efficacy of quinoline derivatives of formula (I). Accordingly, a presence or level of expression of miR-124 may be measured into an isolated biological sample obtained from a patient previously treated with a quinoline derivative of formula (I). Then, the measured presence or level expression of miR-124 into an isolated biological sample may be compared to a control reference value.

When an increase of the measured level relative to the control reference value is observed, then the measure is indicative of an activity of said quinoline derivatives of formula (I).

In another embodiment, when an increase of the measured level relative to the control reference value is observed, then the measure may be indicative of a responsiveness of a patient to a treatment with said quinoline derivatives of formula (I).

In another embodiment, when an increase of the measured level relative to the control reference value is observed, then the measure may be indicative of an effectiveness of a treatment with said quinoline derivatives of formula (I).

In another embodiment, when an increase of the measured level of expression relative to the control reference value is observed, then the measure may be indicative a therapeutic efficacy of said quinoline derivatives of formula (I) as a therapeutic agent for preventing and/or treating a viral infection.

When miR-124 from a sample is "increased" or "up-regulated" after a treatment with a quinoline derivative, as compared to a non-treated control reference value, this increase can be, for example, of about 5%, 10%, 20%, 30%, 40%, 50%, 60%, 70%, 90%, 100%, 200%, 300%, 500%, 1,000%, 5,000% or more of the comparative control reference value (i.e., without the treatment by the quinoline derivative.

In particular, the measured level expression of miR-124 may be at least a two-fold, preferably at least a four-fold, preferably at least a six-fold, preferably at least an eight-fold, and more preferably at least a ten-fold increase relative to said control reference value.

According to another embodiment of the invention, when monitoring a viral infection or assessing an efficacy of a viral infection treatment, in particular with a quinoline derivative of formula (I), a patient may be tested with a method or a use of the invention at a time interval selected from the group consisting of hourly, twice a day, daily, twice a week, weekly, twice a month, monthly, twice a year, yearly, and every other year. The then collected sample can be tested immediately, or can be stored for later testing.

According to another embodiment, use and methods according to the invention may, in particular, allow for the screening, identification or evaluation of potential active agents as a drug candidate.

In particular, use and methods according to the invention are particularly advantageous for the screening, identification or evaluation of potential active agents, such as a drug candidate or a vaccine presumed effective towards a viral infection.

According to another embodiment of the invention, a miR-124 biomarker may be implemented to screen a drug candidate or a vaccine candidate presumed effective for preventing and/or treating a viral infection. In such embodiment, a presence or level of expression of miR-124 may be measured into an isolated biological sample or isolated cell previously contacted with the drug or vaccine to be screened. Then, the obtained measure may be compared to a control reference value.

When an increase of the measured level into an isolated biological sample or isolated cell, previously contacted with the compound, drug or vaccine candidate to be screened, relative to a control reference value is observed, then the measure may be indicative of said candidate to have a biological effect and in particular to be efficient for altering the physiological activity of a cell.

In particular, a drug candidate or vaccine candidate may be characterized as being efficient in preventing and/or treating a viral infection, and in particular a retroviral infection, and more particularly an HIV infection.

When miR-124 from a sample is "increased" or "up-regulated" after treatment with a drug candidate or vaccine, as compared to a non-treated control reference value, this increase can be, for example, of about 5%, 10%, 20%, 30%, 40%, 50%, 60%, 70%, 90%, 100%, 200%, 300%, 500%, 1,000%, 5,000% or more of the comparative control reference value (i.e., without the treatment by the quinoline derivative).

In particular, the measured level expression of miR-124 may be at least a two-fold, preferably at least a four-fold, preferably at least a six-fold, preferably at least an eight-fold, and more preferably at least a ten-fold increase relative to said control reference value.

The uses and methods of the invention may comprise measuring a level of expression of miR-124 into an isolated biological sample. Any suitable sample may be used to assess the miR-124 biomarker.

In particular, a biological sample suitable for the invention may be a biological fluid, such as a blood, a plasma, or a serum, a saliva, an interstitial fluid, or an urine sample; a cell sample, such as a cell culture, a cell line, or a PBMC sample, a tissue biopsy, such as an oral tissue, a gastrointestinal tissue, a skin, an oral mucosa sample, or a plurality of samples from a clinical trial. The sample can be a crude sample, or can be purified to various degrees prior to storage, processing, or measurement.

The step of collecting biological samples for the uses and methods of the invention is performed before carrying out the invention and is not a step of a use or a method in accordance with the invention.

Samples for miRNA assessment can be taken during any desired intervals. For example, samples can be taken hourly, twice per day, daily, weekly, monthly, every other month, yearly, or the like. The sample can be tested immediately, or can be stored for later testing.

The samples can be purified prior to testing. In some embodiments, the miR-124 can be isolated from the remaining cell contents prior to testing. Further, the miR-124 molecules can be separated from the rest of the mRNA in the sample, if desired. For example, the miR-124 can be separated from the mRNA based on size differences prior to testing.

Control reference value to be used for comparing the measured level of expression of miR-124 in a tested biological sample is obtained from a control sample.

Control samples can be taken from various sources. In some embodiments, control samples are taken from the patient prior to treatment or prior to the presence of the disease (such as an archival blood sample). In other embodiments, the control samples are taken from a set of normal, non-diseased members of a population. In another embodiment, a cell assay can be performed on a control cell culture, for example, that has not been treated with the test compound or has been treated with a reference compound, such as the 8-chloro-N-[4-(trifluoromethoxy)phenyl]quinolin-2-amine.

According to one embodiment, for the determination or monitoring of a viral infection in a patient, a control reference value may be obtained from an isolated biological sample obtained on an individual or group of individuals known to not suffer from such condition.

According to another embodiment, for the determination or monitoring of an efficacy of a treatment of a viral infection into a patient, a control reference value may be obtained from an isolated biological sample obtained from an individual or group of individuals known to not suffer from such condition, and not receiving the treatment the efficacy of which is to be determined or monitored. Alternatively, a control reference value may be obtained from an isolated biological sample obtained from a patient suffering from a viral infection and receiving a treatment the efficacy of which being to be determined or monitored, the isolated biological sample being taken from the patient before administration of the treatment.

Numerous methods are available to the skilled man to measure a presence or level of expression of the miR-124 biomarker.

For example, nucleic acid assays or arrays can be used to assess the presence and/or expression level of miR-124 in a sample.

The sequence of the miR-124 may be used to prepare a corresponding nucleotide acting as complementary probe or primer to be used in different nucleic acid assays for detecting the expression or presence of the miR-124 biomarker in the sample, such as, but not limited to, Northern blots and PCR-based methods (e.g., Real-Time Reverse Transcription-PCR or qRT-PCR). Methods such as qRT-PCR may be used to accurately quantitate the amount of the miRNA in a sample.

Sense and anti-sense probes or primers according to the invention may be obtained using every process known to the man skilled in the art, in particular those that are described in Sambrook et al. (Molecular Cloning: A Laboratory Manual, 3$^{rd}$ ED., 2001, Cold Spring Harbour, N.Y.).

Methods related to the detection and quantification of RNA or DNA are well known in the art. The man skilled in the art may for instance refer to Wang et al. (1989, Proc Natl Acad Sci USA, Vol. 86: 917-921), de Wong et al. (2005, Bio Techniques, Vol. 39 (1): 75-85), de Nolan et al. (2006, Nat Protoc, Vol. 1(3): 1559-1582) et de Klinck et al. (2008, Cancer Research, Vol. 68: 657-663), or also to a general review published by Bustin (2000, Journal of Molecular Endocrinology, Vol. 25: 169-193).

In one embodiment, a method for the detection and quantification of nucleic acids may be a fluorescent-dye-based method, wherein nucleic acid concentration is assessed by measuring the fluorescence intensity of ligands, such as dyes, that bind to said nucleic acids. Fluorescent dyes are well known in the art.

Alternatively, said nucleic acid may be quantified using spectrophotometry.

In another embodiment, a method for the detection and quantification of nucleic acids may be a hybridation-based method. Said hybridation-based methods may include PCR and quantitative-PCR (qRT-PCR or q-PCR) techniques or reverse transcriptase/polymerase based techniques. Advantageously, said method may comprise, or be further combined, with a sequencing step.

Those methods may comprise (i) a step of extraction of cellular mRNAs, (ii) a step of reverse transcription of mRNA to DNA using a reverse transcriptase and (iii) a step of DNA amplification from DNA obtained on the previous step. Usually, starting from the same sample, the following nucleic acids are amplified: (a) DNA obtained after a reverse transcription step of the target mRNA and (b) a DNA or a plurality of DNAs obtained after reverse transcription of mRNAs which are constitutively and constantly expressed by cells («housekeeping genes»), such as RNAs coded by genes MRPL19, PUM1 and GADPH.

The amplified DNA can be quantified, after separation by electrophoresis, and measure of DNA bands. Results related to the target mRNA(s) are expressed as relative units in comparison to mRNAs coded by «housekeeping» genes. In some embodiments, the step of separation of amplified DNAs is achieved after agarose gel electrophoresis, and then coloration of DNA bands with ethidium bromide, before quantification of DNA contained in those migration bands with densitometry. In other embodiments, one may use a micro-channel device in which amplified DNA is separated by capillar electrophoresis, before quantification of the emitted signal using a laser beam. Such a device may be a LabChip® device, for instance from the «GX» series, commercialized by the company Caliper LifeSciences (Hopkinton, Mass., USA).

Quantitative results obtained by qRT-PCR can sometimes be more informative than qualitative data, and can simplify assay standardization and quality management. Thus, in some embodiments, qRT-PCR-based assays can be useful to measure miRNA levels during cell-based assays. The qRT-PCR method may be also useful in monitoring patient therapy. Commercially available qRT-PCR based methods {e.g., TaqmanR Array™)

Any suitable assay platform can be used to determine the expression or presence of the miRNA in a sample. For example, an assay may be in the form of a dipstick, a membrane, a chip, a disk, a test strip, a filter, a microsphere, a slide, a multiwell plate, or an optical fiber. An assay system may have a solid support on which an oligonucleotide corresponding to the miRNA is attached. The solid support may comprise, for example, a plastic, silicon, a metal, a resin, glass, a membrane, a particle, a precipitate, a gel, a polymer, a sheet, a sphere, a polysaccharide, a capillary, a film a plate, or a slide. The assay components can be prepared and packaged together as a kit for detecting an miRNA.

In some embodiments, an oligonucleotide array for testing for quinoline derivative or drug candidate activity in a biological sample can be prepared or purchased. An array typically contains a solid support and at least one oligonucleotide contacting the support, where the oligonucleotide corresponds to at least a portion of the miR-124 biomarker. In some embodiments, the portion of the miR-124 biomarker comprises at least 5, 10, 15, 20 or more bases.

According to one embodiment, the presence or expression of miR-124 may be assayed in combination with others miRNA also used as biomarkers. In such an embodiment, an array can be used to assess the expression or presence of multiple miRNAs in a sample, including miRNA-124. In general, the method comprises the following steps: a) contacting the sample with an array comprising a probe set under conditions sufficient for specific binding to occur; and b) examining the array to detect the presence of any detectable label, thereby evaluating the amount of the respective target miRNAs in the sample. The use of an expression array allows obtaining a miRNA expression profile for a given sample.

Methods of preparing assays or arrays for assaying miRNAs are well known in the art and are not needed to be further detailed here.

Nucleic acid arrays can be used to detect presence or differential expression of miRNAs in biological samples. Polynucleotide arrays (such as DNA or RNA arrays) typically include regions of usually different sequence polynucleotides ("capture agents") arranged in a predetermined configuration on a support. The arrays are "addressable" in that these regions (sometimes referenced as "array features") have different predetermined locations ("addresses") on the support of array. The region (i.e., a "feature" or "spot" of the array) at a particular predetermined location (i.e., an "address") on the array will detect a particular miRNA target. The polynucleotide arrays typically are fabricated on planar supports either by depositing previously obtained polynucleotides onto the support in a site specific fashion or by site specific in situ synthesis of the polynucleotides upon the support. Arrays to detect miRNA expression can be fabricated by depositing (e.g., by contact- or jet-based methods or photolithography) either precursor units (such as nucleotide or amino acid monomers) or pre-synthesized capture agent. After depositing the polynucleotide capture agents onto the support, the support is typically processed (e.g., washed and blocked for example) and stored prior to use.

An array to detect miRNA expression has at least two, three, four, or five different subject probes. However, in certain embodiments, a subject array may include a probe set having at least 10, at least 20, at least 50, at least 100, at least 200, at least 500, or at least 1,000 or more probes that can detect a corresponding number of miRNAs. In some embodiments, the subject arrays may include probes for detecting at least a portion or all of the identified miRNAs of an organism, or may include orthologous probes from multiple organisms.

A nucleic acid array may be contacted with a sample or labeled sample containing miRNA analytes under conditions that promote specific binding of the miRNA in the sample to one or more of the capture agents present on the array to exhibit an observed binding pattern. This binding pattern can be detected upon interrogating the array. For example, the target miRNAs in the sample can be labeled with a suitable label (such as a fluorescent compound), and the label then can be accurately observed (such as by observing the fluorescence pattern) on the array after exposure of the array to the sample. The observed binding pattern can be indicative of the presence and/or concentration of one or more miRNA components of the sample.

The labeling of miRNAs may be carried using methods well known in the art, such as using DNA ligase, terminal transferase, or by labeling the RNA backbone, etc. In some embodiments, the miRNAs may be labeled with fluorescent label. Exemplary fluorescent dyes include but are not limited to xanthene dyes, fluorescein dyes, rhodamine dyes, fluorescein isothiocyanate (FITC), 6 carboxyfluorescein (FAM), 6 carboxy-21,41,7',4,7-hexachlorofluorescein (HEX), 6 carboxy 4',5' dichloro 2',7' dimethoxyfluorescein (JOE or J), N,N,N',N' tetramethyl 6 carboxyrhodamine (TAMRA or T), 6 carboxy X rhodamine (ROX or R), carboxyrhodamine 6G (R6G5 or G5), 6 carboxyrhodamine 6G (R6G6 or G6), and rhodamine 110; cyanine dyes, e.g. Cy3, Cy5 and Cy7 dyes; Alexa dyes, e.g. Alexa-fluor-555; coumarin, Diethylaminocoumarin, umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, BODIPY dyes, quinoline dyes, Pyrene, Fluorescein Chlorotriazinyl, R1 10, Eosin, JOE, R6G, Tetramethylrhodamine, Lissamine, ROX, Naptho fluorescein, and the like.

In some embodiments, an oligonucleotide array for assessing immunomodulatory activity can be prepared or purchased, for example from Affymetrix. The array may contain a solid support and a plurality of oligonucleotides contacting the support. The oligonucleotides may be present in specific, addressable locations on the solid support; each corresponding to at least a portion of miRNA sequences which may be differentially expressed upon treatment of a quinoline derivative or a drug candidate in a cell or a patient. The miRNA sequences comprise at least one miR-124 sequence.

When an array is used to assess miRNAs, a typical method can contain the steps of 1) obtaining the array containing surface-bound subject probes; 2) hybridization of a population of miRNAs to the surface-bound probes under conditions sufficient to provide for specific binding (3) post-hybridization washes to remove nucleic acids not bound in the hybridization; and (4) detection of the hybridized miRNAs. The reagents used in each of these steps and their conditions for use may vary depending on the particular application.

Hybridization can be carried out under suitable hybridization conditions, which may vary in stringency as desired. Typical conditions are sufficient to produce probe/target complexes on an array surface between complementary binding members, i.e., between surface-bound subject probes and complementary miRNAs in a sample. In certain embodiments, stringent hybridization conditions may be employed. Hybridization is typically performed under stringent hybridization conditions. Standard hybridization techniques which are well-known in the art (e.g. under conditions sufficient to provide for specific binding of target miRNAs in the sample to the probes on the array) are used to hybridize a sample to a nucleic acid array. Selection of appropriate conditions, including temperature, salt concentration, polynucleotide concentration, hybridization time, stringency of washing conditions, and the like will depend on experimental design, including source of sample, identity of capture agents, degree of complementarity expected, etc., and may be determined as a matter of routine experimentation for those of ordinary skill in the art. In general, a "stringent hybridization" and "stringent hybridization wash conditions" in the context of nucleic acid hybridization are typically sequence dependent, and are different under different experimental conditions. Hybridization may be done over a period of about 12 to about 24 hours. The stringency of the wash conditions can affect the degree to which miRNA sequences are specifically hybridized to complementary capture agents. Those of ordinary skill will readily recognize that alternative but comparable hybridization and wash conditions can be utilized to provide conditions of similar stringency.

As an illustration, in one embodiment, the miRNA expression profiling experiments may be conducted using the Affymetrix Genechip miRNA Array 2.0 and following the protocols described in the instruction manual.

In one particular embodiment, said hybridization can be performed using the GeneChip® Hybridization, Wash, and Stain Kit (Affymetrix Ref. #900720). Advantageously, said hybridization is performed by following the protocols of the manufacturer.

After the miRNA hybridization procedure, the array-surface bound polynucleotides are typically washed to remove unbound nucleic acids. Washing may be performed using any convenient washing protocol, where the washing conditions are typically stringent, as described above. For instance, a washing step may be performed using washing buffers sold by the company Affymetrix (Ref. #900721 and #900722). The hybridization of the target miRNAs to the probes is then detected using standard techniques of reading the array. Reading the resultant hybridized array may be accomplished, for example, by illuminating the array and reading the location and intensity of resulting fluorescence at each feature of the array to detect miRNA/probe binding complexes.

miRNA-124

MicroRNAs (miRNAs) are small, single-stranded non-coding RNAs that can act in the cytoplasm of a cell to cause a decrease in the expression of their cognate target messenger RNAs or translation of the mRNA's protein product. Mature miRNAs are typically about 19-23 nucleotides in length. This ability of miRNAs to inhibit the production of their target proteins results in the regulation of many types of cellular activities, such as cell-fate determination, apoptosis, differentiation, and oncogenesis.

miR-124 was initially cloned in mouse. Human miR-124 precursor (or miRN-124 or miRNA-124 or micro RNA 124) was cloned from embryonic stem cells. 9 haplotypes of miR-124 precursors have been identified so far (Guo et al., PLoS ONE, 2009, 4(11):e7944), from which 3 are present in the Human, hsa-miR-124-1, hsa-miR-124-2 and hsa-miR-124-3. (SEQ ID NO:1 to SEQ ID NO:3).

The miR-124 microRNA precursor is a small non-coding RNA molecule. The mature ~21 nucleotide microRNAs are processed from hairpin precursor sequences by the Dicer enzyme. The mature sequences are SEQ ID NO: 4, UAAGGCACGCGGUGAAUGCC for miR-124-3' and SEQ ID NO: 5, CGUGUUCACAGCGGACCUUGAU for miR-124-5'.

miRNA-124 is preferentially expressed in brain, and could contribute to neurogenesis by downregulating SCP1 expression. Expression of miR124 in mouse neuronal cells induces a switch from general to neuron-specific alternative splicing by directly targeting the mRNA of PTBP1. miR-124 increases the abundance of neuron-specific PTBP2 and Gabbr1 mRNAs by preventing PTBP1-dependent exon skipping that leads to nonsense-mediated decay of these mRNAs.

At the point of mitotic exit within the vertebrate nervous system, when cells lose multipotency and begin to develop stable connections that will persist over life, a switch in ATP-dependent chromatin remodeling mechanisms occurs. This transition could be mediated by repression of BAF53A by miR9* (an miRNA processed from the opposite arm of the miR9 stem-loop precursor) and miR-124.

Experimental autoimmune encephalomyelitis (EAE) is a rodent model of multiple sclerosis characterized by inflammation of the central nervous system (CNS) associated with activation of resident macrophages in the CNS, or microglia, and infiltration of peripheral immune cells to the CNS. It has been found that miR-124 is as highly expressed in microglia and neurons. Expression of miR-124 is reduced in activated microglia during an EAE episode and in activated microglia in culture. Transfection of miR-124 deactivates bone marrow-derived macrophages, and intravenous administration of miR-124 inhibits development of lesions and reduced CNS inflammation in 3 mouse models of EAE. It has been found that miR-124 promotes microglia quiescence by deactivating macrophages via the CEBPA-PU.1 pathway.

It has also been demonstrated that expression miR-124 in human fibroblasts induces their conversion into neurons. Further addition of neurogenic transcription factors ASCL1 and MYT1L enhances the rate of conversion and maturation of the converted neurons, whereas expression of these transcription factors without the aforementioned microRNA is ineffective.

An isolated nucleic acid probe suitable for measuring a presence or level expression of miR-124 is a nucleic acid probe able to specifically hybridize to a miR-124, such as a precursor or a mature miR-124.

Such a nucleic acid probe may comprise from 18 to 30 nucleotides, in particular from 20 to 27, preferably from 20 to 25, preferably from 20, 22, or 25, and more preferably about 25 nucleotides. As previously indicated, such nucleic acid probes may be prepared according to any known methods in the art.

Methods and formulas are well known in the art to predict the optimal hybridization temperature for a given probe and a given target.

Thus, the man skilled in the art may easily calculate an optimal hybridization temperature based on a set of probes, on a given target sequence, and with particular conditions of hybridization.

Advantageously, the optimal hybridization temperature of said probes is between 40° C. and 60° C., and more particularly between 45° C. and 55° C., and preferably is about 48° C.

As examples of buffers useful for hybridizing a nucleic acid probe of the invention to a biomarker of the invention, one may mention, as an hybridization buffer, a buffer comprising 100 mM MES, 1M [Na+], 20 mM EDTA, 0.01% Tween-20, as a non-stringent washing buffer a buffer comprising 6×SSPE, 0.01% Tween-20, and as a stringent washing buffer a buffer comprising 100 mM MES, 0.1M [Na+], 0.01% Tween-20.

A nucleic acid probe suitable for measuring a presence or level expression of miR-124 may, for instance, be a nucleic acid probe consisting in a nucleic acid sequence selected from the group consisting of SEQ ID NO: 6 to SEQ ID NO: 87.

A nucleic acid probe suitable for measuring a presence or level expression of the miR-124-1 precursor may, for instance, be a nucleic acid probe consisting in a nucleic acid sequence selected from the group consisting of SEQ ID NO: 6 to SEQ ID NO: 34, SEQ ID NO 86 and SEQ ID NO 87.

A nucleic acid probe suitable for measuring a presence or level expression of the miR-124-2 precursor may, for instance, be a nucleic acid probe consisting in a nucleic acid sequence selected from the group consisting of SEQ ID NO: 35 to SEQ ID NO: 65, SEQ ID NO 86 and SEQ ID NO 87.

A nucleic acid probe suitable for measuring a presence or level expression of the miR-124-3 precursor may, for instance, be a nucleic acid probe consisting in a nucleic acid sequence selected from the group consisting of SEQ ID NO: 66 to SEQ ID NO: 85, SEQ ID NO 86 and SEQ ID NO 87.

A nucleic acid probe suitable for measuring a presence or level expression of a mature miR-124 may, for instance, be a nucleic acid probe consisting in a nucleic acid sequence selected from the group consisting of SEQ ID NO 86 and SEQ ID NO 87.

Quinoline Derivatives

The quinoline derivatives useful for the invention may be quinoline derivatives efficient for treating a viral infection, such as the ones described in WO 2010/143169.

In particular, the quinoline derivatives useful for the invention are quinoline derivatives which may be represented by the following general formula (I):
wherein

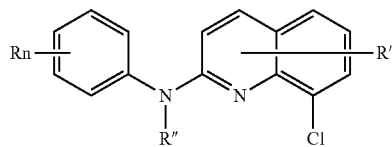
(I)

n is 1 or 2 and R, independently, represents a hydrogen atom, a halogen atom or a group chosen among a $(C_1-C_3)$ alkyl group; a $-NR_1R_2$ group in which $R_1$ and $R_2$ are independently a hydrogen atom or a $(C_1-C_3)$ alkyl group; a $(C_1-C_3)$ fluoroalkoxy group; a $-NO_2$ group; a phenoxy group; and a $(C_1-C_4)$ alkoxy group, R' is a hydrogen atom, a halogen atom or a group chosen among a $(C_1-C_4)$ alkyl group and a $(C_1-C_4)$ alkoxy group, R" is a hydrogen atom or a $(C_1-C_4)$ alkyl group, or one of its pharmaceutically acceptable salt.

According to one embodiment R' and R" are preferably a hydrogen atom.

According to another embodiment, a quinoline derivative suitable for the invention may be of formula (I), in which R independently, represents a halogen atom or a group chosen among a $(C_1-C_3)$ alkyl group; a $-NR_1R_2$ group in which $R_1$ and $R_2$ are independently a hydrogen atom or a $(C_1-C_3)$ alkyl group; a $(C_1-C_3)$ fluoroalkoxy group; and a $(C_1-C_4)$ alkoxy group.

According to another embodiment, R independently, represents a fluorine or a chlorine atom or a group chosen among methyl or ethyl group, a $-NH_2$ group, a methoxy or ethoxy group, and a $(C_1-C_3)$ fluoroalkoxy group.

According to another embodiment, n is preferably 1.

According to a preferred embodiment, a quinoline derivative suitable for the invention may be of formula (I), in which n is 1, R is a $(C_1-C_3)$ fluoroalkoxy group, and R' and R" are each a hydrogen atom.

According to a preferred embodiment, R is a methoxy, an ethoxy, or a propoxy group substituted with at least one fluorine atom. Preferably, R is a mono, bi or trifluoromethoxy group.

Alternatively, the quinoline derivatives useful for the invention are quinoline derivatives which may be represented by a quinoline derivative of formula (II):

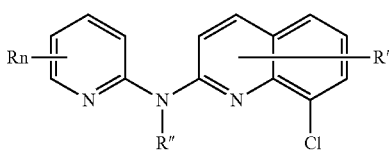
(II)

wherein:

n is 1 or 2 and R, independently, represents a hydrogen atom, a halogen atom or a group chosen among a $(C_1-C_3)$ alkyl group; a $-CN$ group; a hydroxyl group; a $-COOR_1$ group; a $(C_1-C_3)$fluoroalkyl group; a $-NO_2$ group; a $-NR_1R_2$ group with $R_1$ and $R_2$ being a hydrogen atom or a $(C_1-C_3)$alkyl group; and a $(C_1-C_4)$ alkoxy group, R' is a hydrogen atom, a halogen atom or a group chosen among a $(C_1-C_4)$ alkyl group and a $(C_1-C_4)$ alkoxy group, R" is a hydrogen atom or a $(C_1-C_4)$ alkyl group, or one of its pharmaceutically acceptable salt.

According to one embodiment, a quinoline derivative suitable for the invention may be of formula (II), in which R' and R" are preferably a hydrogen atom.

According to another embodiment, a quinoline derivative suitable for the invention may be of formula (II), in which R, independently, represents a hydrogen atom, a halogen atom or a group chosen among a $(C_1-C_3)$ alkyl group, a $(C_1-C_3)$ fluoroalkyl group, a hydroxyl group, a $-CN$ group, a-COOH group and a $(C_1-C_3)$alkoxy group.

According to another embodiment, a quinoline derivative suitable for the invention may be of formula (II), in which R, independently, represents a hydrogen atom, a halogen atom, a $-CN$ group, a $(C_1-C_3)$ alkyl group, a $(C_1-C_3)$ fluoroalkyl group, and a hydroxyl group. According to another embodiment, a quinoline derivative suitable for the invention may be of formula (II), in which R, independently, represents a $(C_1-C_3)$ fluoroalkyl group.

According to another embodiment, n is preferably 1.

According to a preferred embodiment, a quinoline derivative suitable for the invention may be of formula (II), in which n is 1, R is a $(C_1-C_3)$ fluoroalkyl group, and R' and R" are each a hydrogen atom.

Thus, according to said embodiment, a quinoline derivative may be represented by the following formula:

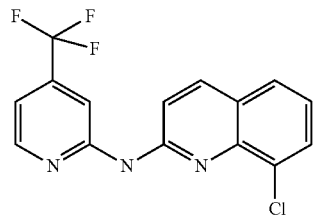 [SMILES: FC(F)(F)c1ccnc(Nc2ccc3cccc(Cl)c3n2)c1]

According to one embodiment, a quinoline derivative useful for the invention, or a salt thereof, may be selected from a group consisting of:

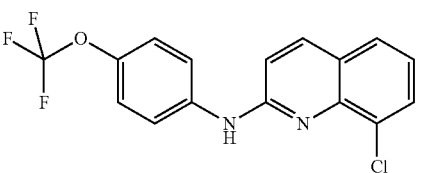 [SMILES: FC(F)(F)Oc1ccc(Nc2ccc3cccc(Cl)c3n2)cc1]
1

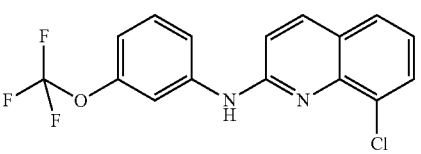
2

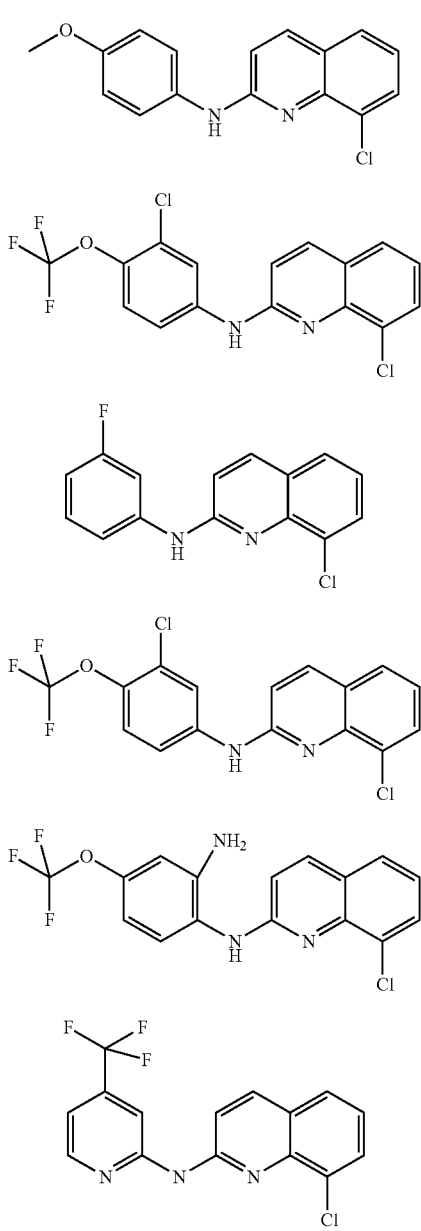

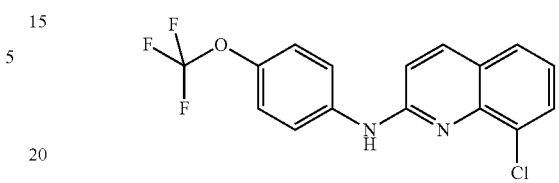

A pharmaceutically acceptable salt of a quinoline derivative of the invention, and more particularly of a compound having the general formula (I) or (II) according to the invention may be a salt of a compound having the general formula (I) or (II) and of an alkali metal, an alkaline earth metal, or a ammonium, comprising the salts obtained with organic ammonium bases, or salts of a compound having the general formula (I) or (II) and of organic or inorganic acid.

Salts more particularly suitable for the invention may be salts of sodium, potassium, calcium, magnesium, quaternary ammonium salts such as tetramethylammonium or tetraethylammonium, and addition salts with ammonia and pharmaceutically acceptable organic amines, such as methylamine, dimethylamine, trimethylamine, ethylamine, triethylamine, ethanolamine and tris(2-hydroxyethyl)amine.

Salts of a quinoline derivative of the invention, and more particularly of a compound having the general formula (I) or (II) and of inorganic acid suitable for the invention may be obtained with hydrochloric acid, hydrobromic acid, sulfuric acid, nitric acid or phosphoric acid.

Salts of a quinoline derivative of the invention, and more particularly of a compound having the general formula (I) or (II) and of organic acid suitable for the invention may be obtained with carboxylic acids and sulfonic acids such as formic acid, acetic acid, oxalic acid, citric acid, lactic acid, malic acid, succinic acid, malonic acid, benzoic acid, maleic acid, fumaric acid, tartaric acid, methanesulfonic acid, benzenesulfonic acid or p-toluenesulfonic acid.

According to a preferred embodiment, the quinoline derivative useful for the invention is 8-chloro-N-[4-(trifluoromethoxy)phenyl]quinolin-2-amine, which may be represented by the following formula:

The quinoline derivatives suitable for the invention may be prepared as described in WO 2010/143169.

The treatment can be oral or parenteral administration of a quinoline derivative. Suitable modes of administration and regimen are described in WO 2010/143169.

Any route of administration may be used. For example, a quinoline derivative can be administered by oral, parenteral, intravenous, transdermal, intramuscular, rectal, sublingual, mucosal, nasal, or other means. In addition, a quinoline derivative can be administered in a form of pharmaceutical composition and/or unit dosage form.

Suitable dosage forms include, but are not limited to, capsules, tablets (including rapid dissolving and delayed release tablets), powder, syrups, oral suspensions and solutions for parenteral administration.

The examples provided herein are intended to be merely exemplary, and those skilled in the art will recognize, or will be able to ascertain using no more than routine experimentation, numerous equivalents of specific compounds, materials, and procedures. All such equivalents are considered to be within the scope of the invention and are encompassed by the appended claims.

EXAMPLES

Example 1

Modulation of miRNAs Expression with 8-chloro-N-[4-(trifluoromethoxy)phenyl]quinolin-2-amine Materials & Methods In the context of HIV-1 inhibition by the quinoline derivative, 8-chloro-N-[4-(trifluoromethoxy)phenyl]quinolin-2-amine, it has been studied if the treatment could modulate host miRNAs expression.

For that purpose, peripheral blood mononuclear cells (PBMCs) of five healthy donors have been isolated by centrifugation on a FICOLL gradient. The cells have then been cultivated at 37° C., 5% $CO_2$ to a density of $1\times10^6$ cells/mL in RPMI Glutamax medium (Life Technologies Ref 61870-010) supplemented with 10% fetal calf serum (FCS) (Thermo Fischer Ref SV30160.03) 1000 U/mL of IL2 (Peprotech Ref 200-02) and 5 mg/mL of PHA (Roche ref 1249738). Three days later, cells have been pooled and resuspended to a density of $1\times10^6$ cells/mL in RPMI Glutamax medium supplemented with 10% fetal calf serum (FCS) 1000 U/mL of IL-2 and distributed in 12 wells plates (Falcon Ref 353043) with 1.2 mL/well (4 wells per condition).

HIV-1 infection has been performed with 1 ng of Ada-M R5 HIV strain/well. Cells were treated for 6 days with 1.2 mL/well of 60 µM solution of 8-chloro-N-[4-(trifluoromethoxy)phenyl]quinolin-2-amine or with 0.12% DMSO (Sigma Ref D4818 as negative control).

Cells were then pooled by conditions, centrifuged, and pellets were resuspended in 700 µL of Qiazol lysis buffer (Qiagen Ref 217004) for miRNeasy kit extraction from Qiagen (Qiagen Ref 217004). RNAs were extracted according to manufacturer's instructions. Extracted RNAs quality and amount were controlled using Agilent Bioanalyzer 2100 and Nanodrop spectrophotometry ND-1000. Mean RIN value was 8.84 (from 7.2 to 9.7). A total RNA amount of 90 ng per sample was labeled using FlashTag™ Biotin HSR RNA Labeling Kit (901911) and hybridized overnight to the Affymetrix Genechip miRNA Array 2.0. (901753) The arrays were washed and stained using standard Affymetrix protocol and scanned using the Affymetrix Scanner. Quality controls were performed using Expression Console metrics from Affymetrix (version 1.2).

Data were normalized using Expression Console "RMA+ DABG" normalization method and a miRNA was considered expressed if the corresponding DABG P-Value was lesser or equal to 0.05. A miRNA was considered expressed in one condition if miRNA was expressed in at least 75% of the PBMCs donors of this condition. A paired Student's t-test was applied on expressed miRNAs that were considered differentially expressed between two conditions if fold-change was greater or equal to 1.5 and T-Test P-Value was lesser or equal to 0.05.

Results

Comparison of miRNA expression between infected and non-infected cells highlighted multiple modification (up or down-regulation) resulting from HIV-1 infection. In particular it is observed that miRNA-124 was down-regulated in HIV infected PBMCs.

In contrast, comparison between 8-chloro-N-[4-(trifluoromethoxy)phenyl]quinolin-2-amine treated or untreated HIV infected PBMCs highlighted only one miRNA, miR-124, whose expression was confidently increased (about 13 fold) under treatment.

Accordingly, miR-124 is validated as being a relevant biomarker to monitor the efficacy of quinoline derivatives according to the invention as anti-viral drugs in AIDS patient, and in particular the 8-chloro-N-[4-(trifluoromethoxy)phenyl]quinolin-2-amine.

Example 2

Evaluation of the Efficiency of Quinoline Derivatives on the Expression of miR-124 3p In addition to Example 1 which provides an assessment of mi-RNA expression in the context of HIV-1 infection, Example 2 assesses the variation of miR-124 expression in the absence of HIV-1. The screening method was tested to evaluate a set of quinoline derivatives and known antiretroviral drugs such as Maraviroc, Efavirenz, Darunavir and azidothymidine (AZT).

Materials & Methods

Extraction of PBMC Using a FICOLL™ Gradient

For that purpose, Peripheral blood mononuclear cells (PBMCs) of four healthy donors have been isolated by centrifugation on a FICOLL™ gradient according to standard protocols.

Briefly, 60-70 mL of buffy-coat are poured in a flask of 175 cm², and the volume is adjusted to 300 mL using PBS in order to obtain a dilution of about 5-fold of the buffy coat. 38 mL of diluted Buffy are then added to Falcon™ tubes of 50 mL comprising 12 mL of FICOLL™ (Histopack-1077) at ambient temperature. The preparation is centrifugated for 30 minutes at 1600 rpm (=515 rcf) at ambient temperature. The lymphocyte ring is recovered from the Falcon™ tube with a transfer pipette (Pastette®) and then washed with PBS using centrifugation for 10 minutes at 1200 rpm (=290 rcf) and at ambient temperature until the supernatant becomes clear.

The cells are then resuspended at 37° C. to a density of 1.5×10⁶ cells/mL in RPMI Glutamax medium (Life Technologies Ref 61870-010) supplemented with 10% fetal calf serum (FCS) (Thermo Fischer Ref SV30160.03) and without activation. Cells are incubated for 48 hours at 37° C. under 5% $CO_2$.

Treatment of Cells with Screened Molecules

Six-well plates are used for the screening. Within each well comprising 3.10⁶ cell/4 ml RPMI supplemented with 10% fetal calf serum and 40 U/mL IL-2 (Peprotech Ref 200-02) are added screened molecules. 100% DMSO (0.8 µL) is added to the well and tested as a negative control.

Each tested condition is set up as described herebelow and the final corresponding volume is adjusted accordingly in the well:

1) Quinoline derivatives: (8-chloro-N-[4-(trifluoromethoxy)phenyl]quinolin-2-amine and 8-chloro-N-[4-(trifluoromethyl)pyridin-2-yl]quinolin-2-amine—Respectively compounds 1 and 8) in 100% DMSO—(5 µM and final volume 0.4 µL):

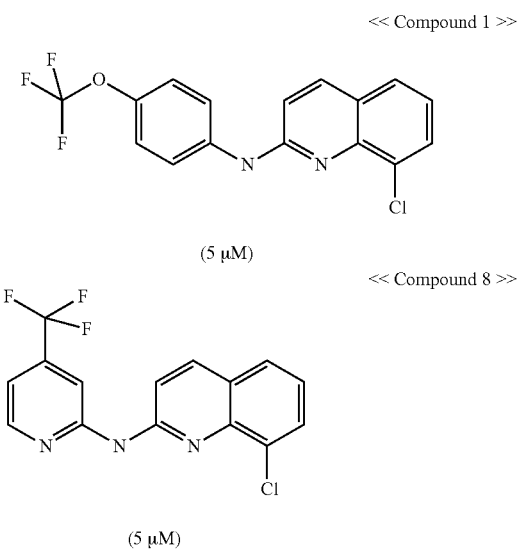

2) Other antiretroviral drugs: Maraviroc, Efavirenz, Darunavir, AZT (10 µM for all—final volume 0.8 µL).

The wells are incubated for three days at 37° C. under 5% $CO_2$. Medium is changed (Day 3) according to standard protocols. Briefly, plates are centrifugated at 1200 rpm for 5 minutes and 3 mL of supernatant is removed. 3 mL of RPMI supplemented with 10% fetal calf serum and 40 U/mL IL-2 is then added with 0.6 µL (for 10 µM final concentration) or 0.3 µL (for 5 µM final concentration) of a stock solution of screened molecule at 50 mM in 100% DMSO or 0.6 µL of 100% DMSO as a negative control.

Extraction of miRNAs (Day 6)

Cells are recovered within Falcon™ tubes of 15 mL, centrifugated at 1200 rpm for 5 minutes, and then washed in 10 mL PBS and further centrifugated at 1200 rpm for 5 minutes. Cells are then resuspended in 1 mL PBS and counted.

$6 \times 10^6$ cells are recovered and centrifugated at 1200 rpm for 5 minutes. The cell pellet is lysed in 300 μL of ML lysis buffer from the Macherey Nagel Nucleospin® miRNA extraction kit (Macherey Nagel Ref 740971), and further stored at −20° C.

5 μL of $2 \times 10^8$ copies/μL of spike-in control (Ce_miR-39 from QIAGEN©—reference 219610, sequence 5' UCACCGGGUGUAAAUCAGCUUG 3' (SEQ ID NO: 88)) are added for each sample. The miRNA extraction is achieved using the protocol from Macherey Nagel Nucleospin® miRNA extraction kit using an elution volume for RNAs of 50 μL and miRNAs of 30 μL, and further stored at −20° C.

Reverse transcription of miRNAs (Day 6)

The reverse transcription step is followed for 12 μL of miRNA using the miScript RT II reverse transcription (RT) kit from QIAGEN© using the miScript HiSpec buffer, and further stored at −20° C.

Quantitative PCR of miRNAs (Day 6)

The quantitative PCR step is achieved using the QIAGEN© miScript SYBR® Green PCR kit and miScript Primer Assays according to the manufacturer's protocol.

Composition of the miScript Reaction Mix for 384-Well Plates:

| Mix | μL/reaction |
| --- | --- |
| 2X SYBR ® Green mix | 5 |
| 10X Universal Primer | 1 |
| 10X Primer Assay | 1 |
| H₂0 | 2 |
| Total Mix volume: | 9 |
| Template cDNA in H₂O (*) | 1 |
| Final volume: | 10 |

(*) cDNA prepared using the miScript II RT kit

The reaction is repeated in triplicates in a 384-well plate according to the manufacturer's protocol on a LightCycler® 380 Roche Real-Time PCR system. Cycling conditions are also set up according to the manufacturer's protocol:

| Step | Time | Temperature |
| --- | --- | --- |
| Initial activation step | 15 min | 95° C. |
| 3-step cycling: | | |
| Denaturation | 15 s | 94° C. |
| Annealing | 30 s | 55° C. |
| Extension | 30 s | 70° C. |
| Cycle number | 40 cycles | |

Relative and Absolute quantification of qPCR are known techniques in the Art and can be achieved as further detailed below.

1) Relative Quantification

From a dilution to the $1/10^{th}$ in H$_2$O for the miR-124 qPCR (Hs_miR-124a) or to the $1/100^{th}$ for reference/housekeeping gene qPCR (Hs_miR-26a and Hs_miR-191, using miScript Primer Assays (Hs_miR-124a, Hs_miR-26a and Hs_miR-191).

The analysis is achieved using relative quantification models without efficiency correction ($2^{-\Delta\Delta Cp}$) using the average of crossing points (Cp) values from triplicates of miR-124 and the average of the average of triplicates of miR-26a and miR-191.

2) Absolute Quantification

From a dilution to the $1/10^{th}$ in H$_2$O for the miR-124 qPCR and miScript Primer Assays (Hs_miR-124a et Ce_miR-39). Calibration curves are achieved according to standard protocols. The analysis is achieved by normalizing the average of miR-124 triplicates with the average of miR-39 triplicates and further normalizing with the number of cells.

RESULTS

Results show good agreement between Relative and Absolute quantification for all molecules. DMSO control samples have a fold-change of 1, meaning no variation in miR-124a expression. All the tested quinoline derivatives show a modulation of miR-124 corresponding to a ten-fold increase of the expression of miR-124.

In comparison, other antiretroviral drugs do not induce significant modulation of the expression of miR-124.

Thus, this Example shows that the miR-124 is a suitable biomarker for screening a drug candidate or vaccine candidate presumed effective in preventing and/or treating a viral infection. It is also particularly useful for assessing the activity of a quinoline derivative of the invention.

The invention claimed is:

1. An in vitro or ex vivo method of measuring miR-124 in a patient with a HIV infection, comprising at least the steps of:
 a. obtaining a biological sample from said patient, said biological sample selected from the group consisting of: a whole blood sample, a swab sample, a plasma sample, a serum sample, a saliva sample, a vaginal fluid sample, a sperm sample, a pharyngeal fluid sample, a bronchial fluid sample, a fecal fluid sample, and a lacrymal fluid sample; and
 b. measuring a presence or expression level of at least miR-124 in the biological sample from said patient,
 wherein measuring the presence or expression level of miR-124 comprises contacting the biological sample with a nucleic acid probe able to specifically hybridize to miR-124, and detecting the hybridization of said probe to miR-124,
 wherein said nucleic acid probe includes a nucleic acid sequence selected from the group consisting of SEQ ID NOS: 6 to 86.

2. The method of claim 1, wherein said biological sample is selected from the group consisting of: a whole blood sample, a plasma sample, and a serum sample.

3. An in vitro or ex vivo method of assessing an activity of a quinoline derivative of formula (I) or (II) or one of their pharmaceutically acceptable salts, for preventing and/or treating a HIV infection in a patient treated with said quinoline derivative, comprising at least the steps of:
 a. measuring a presence or an expression level of at least one miRNA, including miR-124, in a first biological sample previously obtained from said patient before administering said quinoline derivative and in a second biological sample previously obtained from said patient after administering said quinoline derivative; and
 b. determining if said presence or expression level is modulated in the second biological sample obtained after the treatment as compared to the first biological sample obtained before the treatment;
 wherein a modulated presence or expression level of said miRNA is indicative of an activity of said quinoline derivative;
 wherein formula (I) is:

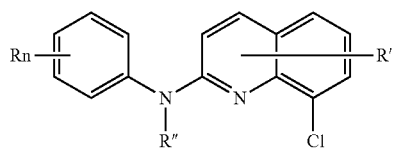

(I)

where:
 n is 1 or 2;
 R independently represents:
  a hydrogen atom,
  a halogen atom,
  a ($C_1$-$C_3$) alkyl group,
  a —$NR_1R_2$ group in which $R_1$ and $R_2$ are independently a hydrogen atom or a ($C_1$-$C_3$) alkyl group,
  a ($C_1$-$C_3$) fluoroalkoxy group,
  a —$NO_2$ group,
  a phenoxy group, or
  a ($C_1$-$C_4$) alkoxy group;
 R' is a hydrogen atom, a halogen atom, a ($C_1$-$C_4$) alkyl group, or a ($C_1$-$C_4$) alkoxy group; and
 R" is a hydrogen atom or a ($C_1$-$C_4$) alkyl group; and
 wherein formula (II) is:

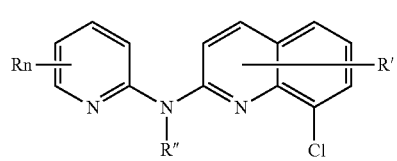

(II)

where:
 n is 1 or 2;
 R independently represents:
  a hydrogen atom,
  a halogen atom,
  a ($C_1$-$C_3$) alkyl group,
  a —CN group,
  a hydroxyl group,
  a —$COOR_1$ group,
  a ($C_1$-$C_3$) fluoroalkyl group,
  a —$NO_2$ group,
  a —$NR_1R_2$ group, or
  a ($C_1$-$C_4$) alkoxy group;
 $R_1$ and $R_2$ are independently a hydrogen atom or a ($C_1$-$C_3$) alkyl group;
 R' is a hydrogen atom, a halogen atom, a ($C_1$-$C_4$) alkyl group, or a ($C_1$-$C_4$) alkoxy group; and
 R" is a hydrogen atom or a ($C_1$-$C_4$) alkyl group.

4. The method of claim 3, wherein said biological sample is selected from the group consisting of a biological tissue sample, a whole blood sample, a swab sample, a plasma sample, a serum sample, a saliva sample, a vaginal fluid sample, a sperm sample, a pharyngeal fluid sample, a bronchial fluid sample, a fecal fluid sample, a cerebrospinal fluid sample, a lacrymal fluid sample, and a tissue culture supernatant sample.

5. The method of claim 3, wherein said patient is tested at a time interval selected from the group consisting of hourly, twice a day, daily, twice a week, weekly, twice a month, monthly, twice a year, yearly, and every other year.

6. The method of claim 3, wherein the quinoline derivative is represented by formula (I) or one of its pharmaceutically acceptable salts where:
n is 1;
R is a ($C_1$-$C_3$) fluoroalkoxy group; and
R' and R" are each a hydrogen atom.

7. The method of claim 6, wherein the quinoline derivative is 8-chloro-N-[4-(trifluoromethoxy)phenyl]quinolin-2-amine.

8. The method of claim 3, wherein the quinoline derivative is represented by formula (II) or one of its pharmaceutically acceptable salts where:
n is 1;
R is a ($C_1$-$C_3$) fluoroalkoxy group; and
R' and R" are each a hydrogen atom.

9. The method of claim 8, wherein the quinoline derivative is 8-chloro-N-[4-(trifluoromethyl)pyridin-2-yl]quinolin-2-amine.

10. The method of claim 3, wherein the quinoline derivative is represented by formula (I) or one of its pharmaceutically acceptable salts.

11. The method of claim 3, wherein the quinoline derivative is represented by formula (II) or one of its pharmaceutically acceptable salts.

12. An in vitro or ex vivo method for measuring miRNA expressed by one or more cells treated with a candidate compound presumed effective in preventing and/or treating a HIV infection, comprising at least the steps of:
a. treating at least one isolated cell able to express at least one miRNA, the at least one miRNA being miR-124, with said candidate compound, said cell being under conditions suitable for expressing said at least one miRNA; and
b. measuring a presence or expression level of said at least one miRNA;
wherein said candidate compound is a quinoline derivative represented by formula (I) or one of its pharmaceutically acceptable salts:

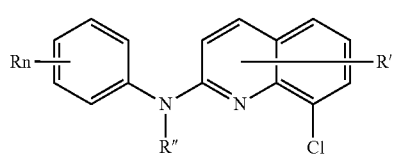

where:
n is 1 or 2;
R independently represents:
  a hydrogen atom,
  a halogen atom,
  a ($C_1$-$C_3$) alkyl group,
  a —$NR_1R_2$ group in which $R_1$ and $R_2$ are independently a hydrogen atom or a ($C_1$-$C_3$) alkyl group,
  a ($C_1$-$C_3$) fluoroalkoxy group,
  a —$NO_2$ group,
  a phenoxy group, or
  a ($C_1$-$C_4$) alkoxy group;
R' is a hydrogen atom, a halogen atom, a ($C_1$-$C_4$) alkyl group, or a ($C_1$-$C_4$) alkoxy group; and
R" is a hydrogen atom or a ($C_1$-$C_4$) alkyl group;

or wherein said candidate compound is a quinoline derivative represented by formula (II) or one of its pharmaceutically acceptable salts:

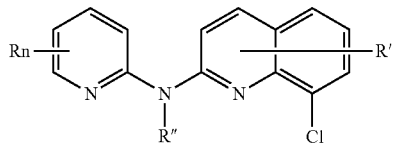

where:
n is 1 or 2;
R independently represents:
  a hydrogen atom,
  a halogen atom,
  a ($C_1$-$C_3$) alkyl group,
  a —CN group,
  a hydroxyl group,
  a —$COOR_1$ group,
  a ($C_1$-$C_3$) fluoroalkyl group,
  a —$NO_2$ group,
  a —$NR_1R_2$ group, or
  a ($C_1$-$C_4$) alkoxy group;
$R_1$ and $R_2$ are independently a hydrogen atom or a ($C_1$-$C_3$) alkyl group;
R' is a hydrogen atom, a halogen atom, a ($C_1$-$C_4$) alkyl group, or a ($C_1$-$C_4$) alkoxy group; and
R" is a hydrogen atom or a ($C_1$-$C_4$) alkyl group.

13. The method of claim 12, further comprising:
c. comparing said measured presence or expression level with a measure or expression level of said at least one miRNA in an untreated isolated cell, wherein:
a modulated presence or expression level of said miRNA is indicative of the efficacy of said candidate compound on a HIV infection; and
said candidate compound is:
(i) a quinoline derivative represented by formula (I) or one of its pharmaceutically acceptable salts:

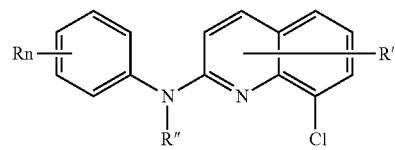

where:
n is 1 or 2;
R independently represents:
  a hydrogen atom,
  a halogen atom,
  a ($C_1$-$C_3$) alkyl group,
  a —$NR_1R_2$ group in which $R_1$ and $R_2$ are independently a hydrogen atom or a ($C_1$-$C_3$) alkyl group,
  a ($C_1$-$C_3$) fluoroalkoxy group,
  a —$NO_2$ group,
  a phenoxy group, or
  a ($C_1$-$C_4$) alkoxy group;
R' is a hydrogen atom, a halogen atom, a ($C_1$-$C_4$) alkyl group, or a ($C_1$-$C_4$) alkoxy group; and
R" is a hydrogen atom or a ($C_1$-$C_4$) alkyl group; or (ii) a quinoline derivative represented by formula (II) or one of its pharmaceutically acceptable salts:

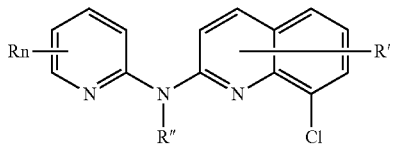

(II)

where:

n is 1 or 2;

R independently represents:
  a hydrogen atom,
  a halogen atom,
  a $(C_1-C_3)$ alkyl group,
  a —CN group,
  a hydroxyl group,
  a —COOR$_1$ group,
  a $(C_1-C_3)$ fluoroalkyl group,
  a —NO$_2$ group,
  a —NR$_1$R$_2$ group, or
  a $(C_1-C_4)$ alkoxy group;

R$_1$ and R$_2$ are independently a hydrogen atom or a $(C_1-C_3)$ alkyl group;

R' is a hydrogen atom, a halogen atom, a $(C_1-C_4)$ alkyl group, or a $(C_1-C_4)$ alkoxy group; and R" is a hydrogen atom or a $(C_1-C_4)$ alkyl group.

14. An in vitro or ex vivo method for measuring miRNA expressed by one or more cells treated with a candidate compound presumed effective in treating a HIV infection, comprising at least the steps of:

a. treating at least one isolated cell able to express at least one miRNA, the at least one miRNA being miR-124, with said candidate compound, said cell being under conditions suitable for expressing said at least one miRNA; and b. measuring a presence or expression level of said at least one miRNA.

* * * * *

SEQUENCE LISTING

```
<160> NUMBER OF SEQ ID NOS: 88

<210> SEQ ID NO 1
<211> LENGTH: 85
<212> TYPE: DNA
<213> ORGANISM: Homo sapiens

<400> SEQUENCE: 1
aggcctctct ctccgtgttc acagcggacc ttgatttaaa tgtccataca attaaggcac    60
gcggtgaatg ccaagaatgg ggctg                                          85

<210> SEQ ID NO 2
<211> LENGTH: 109
<212> TYPE: DNA
<213> ORGANISM: Homo sapiens
```

```
<400> SEQUENCE: 2
atcaagatta gaggctctgc tctccgtgtt cacagcggac cttgatttaa tgtcatacaa    60
ttaaggcacg cggtgaatgc caagagcgga gcctacggct gcacttgaa              109

<210> SEQ ID NO 3
<211> LENGTH: 87
<212> TYPE: DNA
<213> ORGANISM: Homo sapiens

<400> SEQUENCE: 3
tgagggcccc tctgcgtgtt cacagcggac cttgatttaa tgtctataca attaaggcac    60
gcggtgaatg ccaagagagg cgcctcc                                       87

<210> SEQ ID NO 4
<211> LENGTH: 20
<212> TYPE: RNA
<213> ORGANISM: Homo sapiens

<400> SEQUENCE: 4
uaaggcacgc ggugaaugcc                                               20

<210> SEQ ID NO 5
<211> LENGTH: 22
<212> TYPE: RNA
<213> ORGANISM: Homo sapiens

<400> SEQUENCE: 5
cguguucaca gcggaccuug au                                            22

<210> SEQ ID NO 6
<211> LENGTH: 25
<212> TYPE: DNA
<213> ORGANISM: Artificial Sequence
<220> FEATURE:
<223> OTHER INFORMATION: probe

<400> SEQUENCE: 6
gcacaagtgt cgcctggaac taaat                                         25

<210> SEQ ID NO 7
<211> LENGTH: 25
<212> TYPE: DNA
<213> ORGANISM: Artificial Sequence
<220> FEATURE:
<223> OTHER INFORMATION: probe

<400> SEQUENCE: 7
cacaagtgtc gcctggaact aaatt                                         25

<210> SEQ ID NO 8
<211> LENGTH: 25
<212> TYPE: DNA
<213> ORGANISM: Artificial Sequence
<220> FEATURE:
<223> OTHER INFORMATION: probe

<400> SEQUENCE: 8
tatgttaatt ccgtgcgcca cttac                                         25

<210> SEQ ID NO 9
<211> LENGTH: 25
<212> TYPE: DNA
<213> ORGANISM: Artificial Sequence
```

```
<220> FEATURE:
<223> OTHER INFORMATION: probe

<400> SEQUENCE: 9
atgttaattc cgtgcgccac ttacg                                          25

<210> SEQ ID NO 10
<211> LENGTH: 25
<212> TYPE: DNA
<213> ORGANISM: Artificial Sequence
<220> FEATURE:
<223> OTHER INFORMATION: probe

<400> SEQUENCE: 10
tgttaattcc gtgcgccact tacgg                                          25

<210> SEQ ID NO 11
<211> LENGTH: 25
<212> TYPE: DNA
<213> ORGANISM: Artificial Sequence
<220> FEATURE:
<223> OTHER INFORMATION: probe

<400> SEQUENCE: 11
gttaattccg tgcgccactt acggt                                          25

<210> SEQ ID NO 12
<211> LENGTH: 25
<212> TYPE: DNA
<213> ORGANISM: Artificial Sequence
<220> FEATURE:
<223> OTHER INFORMATION: probe

<400> SEQUENCE: 12
ttaattccgt gcgccactta cggtt                                          25

<210> SEQ ID NO 13
<211> LENGTH: 25
<212> TYPE: DNA
<213> ORGANISM: Artificial Sequence
<220> FEATURE:
<223> OTHER INFORMATION: probe

<400> SEQUENCE: 13
taattccgtg cgccacttac ggttc                                          25

<210> SEQ ID NO 14
<211> LENGTH: 25
<212> TYPE: DNA
<213> ORGANISM: Artificial Sequence
<220> FEATURE:
<223> OTHER INFORMATION: probe

<400> SEQUENCE: 14
aattccgtgc gccacttacg gttct                                          25

<210> SEQ ID NO 15
<211> LENGTH: 25
<212> TYPE: DNA
<213> ORGANISM: Artificial Sequence
<220> FEATURE:
<223> OTHER INFORMATION: probe

<400> SEQUENCE: 15
gcctggaact aaatttacag gtatg                                          25
```

```
<210> SEQ ID NO 16
<211> LENGTH: 25
<212> TYPE: DNA
<213> ORGANISM: Artificial Sequence
<220> FEATURE:
<223> OTHER INFORMATION: probe

<400> SEQUENCE: 16
cctggaacta aatttacagg tatgt                                        25

<210> SEQ ID NO 17
<211> LENGTH: 25
<212> TYPE: DNA
<213> ORGANISM: Artificial Sequence
<220> FEATURE:
<223> OTHER INFORMATION: probe

<400> SEQUENCE: 17
ctggaactaa atttacaggt atgtt                                        25

<210> SEQ ID NO 18
<211> LENGTH: 25
<212> TYPE: DNA
<213> ORGANISM: Artificial Sequence
<220> FEATURE:
<223> OTHER INFORMATION: probe

<400> SEQUENCE: 18
ggaactaaat ttacaggtat gttaa                                        25

<210> SEQ ID NO 19
<211> LENGTH: 25
<212> TYPE: DNA
<213> ORGANISM: Artificial Sequence
<220> FEATURE:
<223> OTHER INFORMATION: probe

<400> SEQUENCE: 19
gaactaaatt tacaggtatg ttaat                                        25

<210> SEQ ID NO 20
<211> LENGTH: 25
<212> TYPE: DNA
<213> ORGANISM: Artificial Sequence
<220> FEATURE:
<223> OTHER INFORMATION: probe

<400> SEQUENCE: 20
aactaaattt acaggtatgt taatt                                        25

<210> SEQ ID NO 21
<211> LENGTH: 25
<212> TYPE: DNA
<213> ORGANISM: Artificial Sequence
<220> FEATURE:
<223> OTHER INFORMATION: probe

<400> SEQUENCE: 21
ctaaatttac aggtatgtta attcc                                        25

<210> SEQ ID NO 22
<211> LENGTH: 25
<212> TYPE: DNA
<213> ORGANISM: Artificial Sequence
<220> FEATURE:
<223> OTHER INFORMATION: probe
```

<400> SEQUENCE: 22
taaatttaca ggtatgttaa ttccg    25

<210> SEQ ID NO 23
<211> LENGTH: 25
<212> TYPE: DNA
<213> ORGANISM: Artificial Sequence
<220> FEATURE:
<223> OTHER INFORMATION: probe

<400> SEQUENCE: 23
aaatttacag gtatgttaat tccgt    25

<210> SEQ ID NO 24
<211> LENGTH: 25
<212> TYPE: DNA
<213> ORGANISM: Artificial Sequence
<220> FEATURE:
<223> OTHER INFORMATION: probe

<400> SEQUENCE: 24
tccggagaga gaggcacaag tgtcg    25

<210> SEQ ID NO 25
<211> LENGTH: 25
<212> TYPE: DNA
<213> ORGANISM: Artificial Sequence
<220> FEATURE:
<223> OTHER INFORMATION: probe

<400> SEQUENCE: 25
agagaggcac aagtgtcgcc tggaa    25

<210> SEQ ID NO 26
<211> LENGTH: 25
<212> TYPE: DNA
<213> ORGANISM: Artificial Sequence
<220> FEATURE:
<223> OTHER INFORMATION: probe

<400> SEQUENCE: 26
acaagtgtcg cctggaacta aattt    25

<210> SEQ ID NO 27
<211> LENGTH: 25
<212> TYPE: DNA
<213> ORGANISM: Artificial Sequence
<220> FEATURE:
<223> OTHER INFORMATION: probe

<400> SEQUENCE: 27
gcctggaact aaatttacag gtatg    25

<210> SEQ ID NO 28
<211> LENGTH: 25
<212> TYPE: DNA
<213> ORGANISM: Artificial Sequence
<220> FEATURE:
<223> OTHER INFORMATION: probe

<400> SEQUENCE: 28
ctggaactaa atttacaggt atgtt    25

```
<210> SEQ ID NO 29
<211> LENGTH: 25
<212> TYPE: DNA
<213> ORGANISM: Artificial Sequence
<220> FEATURE:
<223> OTHER INFORMATION: probe

<400> SEQUENCE: 29
ggaactaaat ttacaggtat gttaa                                    25

<210> SEQ ID NO 30
<211> LENGTH: 25
<212> TYPE: DNA
<213> ORGANISM: Artificial Sequence
<220> FEATURE:
<223> OTHER INFORMATION: probe

<400> SEQUENCE: 30
taaatttaca ggtatgttaa ttccg                                    25

<210> SEQ ID NO 31
<211> LENGTH: 25
<212> TYPE: DNA
<213> ORGANISM: Artificial Sequence
<220> FEATURE:
<223> OTHER INFORMATION: probe

<400> SEQUENCE: 31
aaatttacag gtatgttaat tccgt                                    25

<210> SEQ ID NO 32
<211> LENGTH: 25
<212> TYPE: DNA
<213> ORGANISM: Artificial Sequence
<220> FEATURE:
<223> OTHER INFORMATION: probe

<400> SEQUENCE: 32
caggtatgtt aattccgtgc gccac                                    25

<210> SEQ ID NO 33
<211> LENGTH: 25
<212> TYPE: DNA
<213> ORGANISM: Artificial Sequence
<220> FEATURE:
<223> OTHER INFORMATION: probe

<400> SEQUENCE: 33
ggtatgttaa ttccgtgcgc cactt                                    25

<210> SEQ ID NO 34
<211> LENGTH: 25
<212> TYPE: DNA
<213> ORGANISM: Artificial Sequence
<220> FEATURE:
<223> OTHER INFORMATION: probe

<400> SEQUENCE: 34
ttccgtgcgc cacttacggt tctta                                    25

<210> SEQ ID NO 35
<211> LENGTH: 25
<212> TYPE: DNA
<213> ORGANISM: Artificial Sequence
<220> FEATURE:
<223> OTHER INFORMATION: probe
```

<400> SEQUENCE: 35
gcacaagtgt cgcctggaac taaat        25

<210> SEQ ID NO 36
<211> LENGTH: 25
<212> TYPE: DNA
<213> ORGANISM: Artificial Sequence
<220> FEATURE:
<223> OTHER INFORMATION: probe

<400> SEQUENCE: 36
tatgttaatt ccgtgcgcca cttac        25

<210> SEQ ID NO 37
<211> LENGTH: 25
<212> TYPE: DNA
<213> ORGANISM: Artificial Sequence
<220> FEATURE:
<223> OTHER INFORMATION: probe

<400> SEQUENCE: 37
cacaagtgtc gcctggaact aaatt        25

<210> SEQ ID NO 38
<211> LENGTH: 25
<212> TYPE: DNA
<213> ORGANISM: Artificial Sequence
<220> FEATURE:
<223> OTHER INFORMATION: probe

<400> SEQUENCE: 38
atgttaattc cgtgcgccac ttacg        25

<210> SEQ ID NO 39
<211> LENGTH: 25
<212> TYPE: DNA
<213> ORGANISM: Artificial Sequence
<220> FEATURE:
<223> OTHER INFORMATION: probe

<400> SEQUENCE: 39
tgttaattcc gtgcgccact tacgg        25

<210> SEQ ID NO 40
<211> LENGTH: 25
<212> TYPE: DNA
<213> ORGANISM: Artificial Sequence
<220> FEATURE:
<223> OTHER INFORMATION: probe

<400> SEQUENCE: 40
gttaattccg tgcgccactt acggt        25

<210> SEQ ID NO 41
<211> LENGTH: 25
<212> TYPE: DNA
<213> ORGANISM: Artificial Sequence
<220> FEATURE:
<223> OTHER INFORMATION: probe

<400> SEQUENCE: 41
ttaattccgt gcgccactta cggtt        25

```
<210> SEQ ID NO 42
<211> LENGTH: 25
<212> TYPE: DNA
<213> ORGANISM: Artificial Sequence
<220> FEATURE:
<223> OTHER INFORMATION: probe

<400> SEQUENCE: 42
taattccgtg cgccacttac ggttc                                   25

<210> SEQ ID NO 43
<211> LENGTH: 25
<212> TYPE: DNA
<213> ORGANISM: Artificial Sequence
<220> FEATURE:
<223> OTHER INFORMATION: probe

<400> SEQUENCE: 43
aattccgtgc gccacttacg gttct                                   25

<210> SEQ ID NO 44
<211> LENGTH: 25
<212> TYPE: DNA
<213> ORGANISM: Artificial Sequence
<220> FEATURE:
<223> OTHER INFORMATION: probe

<400> SEQUENCE: 44
tagttctaat ctccgagacg agagg                                   25

<210> SEQ ID NO 45
<211> LENGTH: 25
<212> TYPE: DNA
<213> ORGANISM: Artificial Sequence
<220> FEATURE:
<223> OTHER INFORMATION: probe

<400> SEQUENCE: 45
ccacttacgg ttctcgcctc ggatg                                   25

<210> SEQ ID NO 46
<211> LENGTH: 25
<212> TYPE: DNA
<213> ORGANISM: Artificial Sequence
<220> FEATURE:
<223> OTHER INFORMATION: probe

<400> SEQUENCE: 46
gttctaatct ccgagacgag aggca                                   25

<210> SEQ ID NO 47
<211> LENGTH: 25
<212> TYPE: DNA
<213> ORGANISM: Artificial Sequence
<220> FEATURE:
<223> OTHER INFORMATION: probe

<400> SEQUENCE: 47
acttacggtt ctcgcctcgg atgcc                                   25

<210> SEQ ID NO 48
<211> LENGTH: 25
<212> TYPE: DNA
<213> ORGANISM: Artificial Sequence
<220> FEATURE:
<223> OTHER INFORMATION: probe
```

```
<400> SEQUENCE: 48
tctaatctcc gagacgagag gcaca                                              25

<210> SEQ ID NO 49
<211> LENGTH: 25
<212> TYPE: DNA
<213> ORGANISM: Artificial Sequence
<220> FEATURE:
<223> OTHER INFORMATION: probe

<400> SEQUENCE: 49
tacggttctc gcctcggatg ccgac                                              25

<210> SEQ ID NO 50
<211> LENGTH: 25
<212> TYPE: DNA
<213> ORGANISM: Artificial Sequence
<220> FEATURE:
<223> OTHER INFORMATION: probe

<400> SEQUENCE: 50
aatctccgag acgagaggca caagt                                              25

<210> SEQ ID NO 51
<211> LENGTH: 25
<212> TYPE: DNA
<213> ORGANISM: Artificial Sequence
<220> FEATURE:
<223> OTHER INFORMATION: probe

<400> SEQUENCE: 51
ttctcgcctc ggatgccgac gtgaa                                              25

<210> SEQ ID NO 52
<211> LENGTH: 25
<212> TYPE: DNA
<213> ORGANISM: Artificial Sequence
<220> FEATURE:
<223> OTHER INFORMATION: probe

<400> SEQUENCE: 52
tctccgagac gagaggcaca agtgt                                              25

<210> SEQ ID NO 53
<211> LENGTH: 25
<212> TYPE: DNA
<213> ORGANISM: Artificial Sequence
<220> FEATURE:
<223> OTHER INFORMATION: probe

<400> SEQUENCE: 53
ctcgcctcgg atgccgacgt gaact                                              25

<210> SEQ ID NO 54
<211> LENGTH: 25
<212> TYPE: DNA
<213> ORGANISM: Artificial Sequence
<220> FEATURE:
<223> OTHER INFORMATION: probe

<400> SEQUENCE: 54
tcgcctcgga tgccgacgtg aactt                                              25
```

<210> SEQ ID NO 55
<211> LENGTH: 25
<212> TYPE: DNA
<213> ORGANISM: Artificial Sequence
<220> FEATURE:
<223> OTHER INFORMATION: probe

<400> SEQUENCE: 55
tagttctaat ctccgagacg agagg                                          25

<210> SEQ ID NO 56
<211> LENGTH: 25
<212> TYPE: DNA
<213> ORGANISM: Artificial Sequence
<220> FEATURE:
<223> OTHER INFORMATION: probe

<400> SEQUENCE: 56
tctaatctcc gagacgagag gcaca                                          25

<210> SEQ ID NO 57
<211> LENGTH: 25
<212> TYPE: DNA
<213> ORGANISM: Artificial Sequence
<220> FEATURE:
<223> OTHER INFORMATION: probe

<400> SEQUENCE: 57
aatctccgag acgagaggca caagt                                          25

<210> SEQ ID NO 58
<211> LENGTH: 25
<212> TYPE: DNA
<213> ORGANISM: Artificial Sequence
<220> FEATURE:
<223> OTHER INFORMATION: probe

<400> SEQUENCE: 58
tctccgagac gagaggcaca agtgt                                          25

<210> SEQ ID NO 59
<211> LENGTH: 25
<212> TYPE: DNA
<213> ORGANISM: Artificial Sequence
<220> FEATURE:
<223> OTHER INFORMATION: probe

<400> SEQUENCE: 59
acaagtgtcg cctggaacta aatta                                          25

<210> SEQ ID NO 60
<211> LENGTH: 25
<212> TYPE: DNA
<213> ORGANISM: Artificial Sequence
<220> FEATURE:
<223> OTHER INFORMATION: probe

<400> SEQUENCE: 60
acagtatgtt aattccgtgc gccac                                          25

<210> SEQ ID NO 61
<211> LENGTH: 25
<212> TYPE: DNA
<213> ORGANISM: Artificial Sequence
<220> FEATURE:
<223> OTHER INFORMATION: probe

```
<400> SEQUENCE: 61
ccacttacgg ttctcgcctc ggatg                                              25

<210> SEQ ID NO 62
<211> LENGTH: 25
<212> TYPE: DNA
<213> ORGANISM: Artificial Sequence
<220> FEATURE:
<223> OTHER INFORMATION: probe

<400> SEQUENCE: 62
acttacggtt ctcgcctcgg atgcc                                              25

<210> SEQ ID NO 63
<211> LENGTH: 25
<212> TYPE: DNA
<213> ORGANISM: Artificial Sequence
<220> FEATURE:
<223> OTHER INFORMATION: probe

<400> SEQUENCE: 63
tacggttctc gcctcggatg ccgac                                              25

<210> SEQ ID NO 64
<211> LENGTH: 25
<212> TYPE: DNA
<213> ORGANISM: Artificial Sequence
<220> FEATURE:
<223> OTHER INFORMATION: probe

<400> SEQUENCE: 64
ttctcgcctc ggatgccgac gtgaa                                              25

<210> SEQ ID NO 65
<211> LENGTH: 25
<212> TYPE: DNA
<213> ORGANISM: Artificial Sequence
<220> FEATURE:
<223> OTHER INFORMATION: probe

<400> SEQUENCE: 65
ctcgcctcgg atgccgacgt gaact                                              25

<210> SEQ ID NO 66
<211> LENGTH: 25
<212> TYPE: DNA
<213> ORGANISM: Artificial Sequence
<220> FEATURE:
<223> OTHER INFORMATION: probe

<400> SEQUENCE: 66
gcacaagtgt cgcctggaac taaat                                              25

<210> SEQ ID NO 67
<211> LENGTH: 25
<212> TYPE: DNA
<213> ORGANISM: Artificial Sequence
<220> FEATURE:
<223> OTHER INFORMATION: probe

<400> SEQUENCE: 67
tatgttaatt ccgtgcgcca cttac                                              25
```

```
<210> SEQ ID NO 68
<211> LENGTH: 25
<212> TYPE: DNA
<213> ORGANISM: Artificial Sequence
<220> FEATURE:
<223> OTHER INFORMATION: probe

<400> SEQUENCE: 68
cacaagtgtc gcctggaact aaatt                                          25

<210> SEQ ID NO 69
<211> LENGTH: 25
<212> TYPE: DNA
<213> ORGANISM: Artificial Sequence
<220> FEATURE:
<223> OTHER INFORMATION: probe

<400> SEQUENCE: 69
atgttaattc cgtgcgccac ttacg                                          25

<210> SEQ ID NO 70
<211> LENGTH: 25
<212> TYPE: DNA
<213> ORGANISM: Artificial Sequence
<220> FEATURE:
<223> OTHER INFORMATION: probe

<400> SEQUENCE: 70
tgttaattcc gtgcgccact tacgg                                          25

<210> SEQ ID NO 71
<211> LENGTH: 25
<212> TYPE: DNA
<213> ORGANISM: Artificial Sequence
<220> FEATURE:
<223> OTHER INFORMATION: probe

<400> SEQUENCE: 71
gttaattccg tgcgccactt acggt                                          25

<210> SEQ ID NO 72
<211> LENGTH: 25
<212> TYPE: DNA
<213> ORGANISM: Artificial Sequence
<220> FEATURE:
<223> OTHER INFORMATION: probe

<400> SEQUENCE: 72
ttaattccgt gcgccactta cggtt                                          25

<210> SEQ ID NO 73
<211> LENGTH: 25
<212> TYPE: DNA
<213> ORGANISM: Artificial Sequence
<220> FEATURE:
<223> OTHER INFORMATION: probe

<400> SEQUENCE: 73
taattccgtg cgccacttac ggttc                                          25

<210> SEQ ID NO 74
<211> LENGTH: 25
<212> TYPE: DNA
<213> ORGANISM: Artificial Sequence
<220> FEATURE:
<223> OTHER INFORMATION: probe
```

<400> SEQUENCE: 74
aattccgtgc gccacttacg gttct                                    25

<210> SEQ ID NO 75
<211> LENGTH: 25
<212> TYPE: DNA
<213> ORGANISM: Artificial Sequence
<220> FEATURE:
<223> OTHER INFORMATION: probe

<400> SEQUENCE: 75
actcccgggg agacgcacaa gtgtc                                    25

<210> SEQ ID NO 76
<211> LENGTH: 25
<212> TYPE: DNA
<213> ORGANISM: Artificial Sequence
<220> FEATURE:
<223> OTHER INFORMATION: probe

<400> SEQUENCE: 76
ctcccgggga gacgcacaag tgtcg                                    25

<210> SEQ ID NO 77
<211> LENGTH: 25
<212> TYPE: DNA
<213> ORGANISM: Artificial Sequence
<220> FEATURE:
<223> OTHER INFORMATION: probe

<400> SEQUENCE: 77
ccggggagac gcacaagtgt cgcct                                    25

<210> SEQ ID NO 78
<211> LENGTH: 25
<212> TYPE: DNA
<213> ORGANISM: Artificial Sequence
<220> FEATURE:
<223> OTHER INFORMATION: probe

<400> SEQUENCE: 78
acgcacaagt gtcgcctgga actaa                                    25

<210> SEQ ID NO 79
<211> LENGTH: 25
<212> TYPE: DNA
<213> ORGANISM: Artificial Sequence
<220> FEATURE:
<223> OTHER INFORMATION: probe

<400> SEQUENCE: 79
gtgtcgcctg gaactaaatt acaga                                    25

<210> SEQ ID NO 80
<211> LENGTH: 25
<212> TYPE: DNA
<213> ORGANISM: Artificial Sequence
<220> FEATURE:
<223> OTHER INFORMATION: probe

<400> SEQUENCE: 80
gcctggaact aaattacaga tatgt                                    25

```
<210> SEQ ID NO 81
<211> LENGTH: 25
<212> TYPE: DNA
<213> ORGANISM: Artificial Sequence
<220> FEATURE:
<223> OTHER INFORMATION: probe

<400> SEQUENCE: 81
ttacagatat gttaattccg tgcgc                                          25

<210> SEQ ID NO 82
<211> LENGTH: 25
<212> TYPE: DNA
<213> ORGANISM: Artificial Sequence
<220> FEATURE:
<223> OTHER INFORMATION: probe

<400> SEQUENCE: 82
agatatgtta attccgtgcg ccact                                          25

<210> SEQ ID NO 83
<211> LENGTH: 25
<212> TYPE: DNA
<213> ORGANISM: Artificial Sequence
<220> FEATURE:
<223> OTHER INFORMATION: probe

<400> SEQUENCE: 83
ttccgtgcgc cacttacggt tctct                                          25

<210> SEQ ID NO 84
<211> LENGTH: 25
<212> TYPE: DNA
<213> ORGANISM: Artificial Sequence
<220> FEATURE:
<223> OTHER INFORMATION: probe

<400> SEQUENCE: 84
gccacttacg gttctctccg cggag                                          25

<210> SEQ ID NO 85
<211> LENGTH: 25
<212> TYPE: DNA
<213> ORGANISM: Artificial Sequence
<220> FEATURE:
<223> OTHER INFORMATION: probe

<400> SEQUENCE: 85
ccacttacgg ttctctccgc ggagg                                          25

<210> SEQ ID NO 86
<211> LENGTH: 22
<212> TYPE: DNA
<213> ORGANISM: Artificial Sequence
<220> FEATURE:
<223> OTHER INFORMATION: probe

<400> SEQUENCE: 86
gcacaagtgt cgcctggaac ta                                             22

<210> SEQ ID NO 87
<211> LENGTH: 20
<212> TYPE: DNA
<213> ORGANISM: Artificial Sequence
<220> FEATURE:
<223> OTHER INFORMATION: probe
```

-continued

```
<400> SEQUENCE: 87
attccgtgcg ccacttacgg                                                    20

<210> SEQ ID NO 88
<211> LENGTH: 22
<212> TYPE: RNA
<213> ORGANISM: Artificial Sequence
<220> FEATURE:
<223> OTHER INFORMATION: control

<400> SEQUENCE: 88
ucaccgggug uaaaucagcu ug                                                 22
```